(12) United States Patent
Meijer et al.

(10) Patent No.: US 8,552,053 B2
(45) Date of Patent: Oct. 8, 2013

(54) 7-SUBSTITUTED INDIRUBIN-3'OXIMES AND THEIR APPLICATIONS

(75) Inventors: Laurent Meijer, Roscoff (FR); Karima Bettayeb, Roscoff (FR); Alexios-Le-Andros Skaltsounis, Athens (GR); Prokopios Maglatis, Ambelakia (GR); Jacint Boix, Lleida (ES); Judit Ribas, Vilanova de la Barea (ES)

(73) Assignees: Centre National de la Recherche Scientifique, Paris Cedex (FR); University of Pierre and Marie Curie (Paris 6), Paris Cedex (FR); University of Rennes 1, Rennes Cedex (FR); University of Lleida, Lleida (ES); Universite d'Athenes, Athens (GR)

( * ) Notice: Subject to any disclaimer, the term of this patent is extended or adjusted under 35 U.S.C. 154(b) by 781 days.

(21) Appl. No.: 12/086,984

(22) PCT Filed: Dec. 21, 2006

(86) PCT No.: PCT/IB2006/004152
§ 371 (c)(1),
(2), (4) Date: Sep. 20, 2010

(87) PCT Pub. No.: WO2007/099402
PCT Pub. Date: Sep. 7, 2007

(65) Prior Publication Data
US 2010/0331327 A1 Dec. 30, 2010

Related U.S. Application Data

(60) Provisional application No. 60/752,874, filed on Dec. 23, 2005, provisional application No. 60/785,377, filed on Mar. 24, 2006.

(51) Int. Cl.
*A61K 31/40* (2006.01)
*C09B 7/04* (2006.01)

(52) U.S. Cl.
USPC .......................... 514/418; 514/414; 548/459

(58) Field of Classification Search
None
See application file for complete search history.

(56) References Cited

U.S. PATENT DOCUMENTS

| 6,987,092 B1 * | 1/2006 | Eisenbrand et al. ............ 514/25 |
| 2007/0276025 A1 | 11/2007 | Meijer |
| 2010/0331327 A1 | 12/2010 | Meijer et al. |
| 2011/0136808 A1 | 6/2011 | Meijer et al. |

FOREIGN PATENT DOCUMENTS

WO 2005/041954 5/2005

OTHER PUBLICATIONS

Polychronopoulos et al., "Structural bases for the synthesis of Indirubins as potent and selective inhibitors of glycogen synthase kinase-3 and cyclin dependent kinases", *Journal of Medicinal Chemistry*, vol. 47, 2004, pp. 935-946, XP002453468.
Meijer et al., "GSK-3-Selective inhibitors derived from Tyrian Purple Indirubins", *Chemistry & Biology*, vol. 10, 2003, pp. 1255-1266, XP002453469.
Ribas et al, "7-Bromindirubin-3'-oxime induces capase-independent cell death", *Oncogene*, vol. 25, No. 47, 2006, pp. 6304-6318, XP002453470.
Ferandin et al., "3'-Substituted 7-Halogenoindirubins, a New Class of Cell Death Inducing Agents", *Journal of Medicinal Chemistry*, vol. 49, No. 15, 2006, pp. 4638-4649, XP002453471.
International Search Report for PCT/IB2006/004152, mailed Oct. 23, 2007.
K. Vougogiannopoulou et al., "Soluble 3', 6-substituted Indirubins with Enchanced Selectivity towards Glycogen Synthase Kinase-3 Alter Circadian Period", J. Med. Chem., vol. 51, No. 20, Sep. 25, 2008, pp. 6421-6431.
Ferandin et al, Document No. 145:271522 (2006), retrieved from CAPLUS.
Olivier et al, Document No. 150:162202 (2008), retrieved from CAPLUS.
Cecil Textbook of Medicine, $20^{th}$ edition (1996), vol. 2, pp. 2050-2057.
Cecil Textbook of Medicine, $20^{th}$ edition (1996), vol. 2, pp. 1992-1996.
CNN.com—FDA mulls drug to slow late-stage Alzheimer's [online], [retrieved on Sep. 23, 2003], Retrieved from the Internet, URL; http://www.cnn.com/2003/HEALTH/conditions/09/24/alzheimers.drug.ap/index.html>.

* cited by examiner

*Primary Examiner* — Sreeni Padmanabhan
*Assistant Examiner* — Jody Karol
(74) *Attorney, Agent, or Firm* — Nixon & Vanderhye P.C.

(57) ABSTRACT

The invention relates to new 3'-, 7-substituted-indirubins of formula (I) wherein R represents N—OH, N—O-alkyl or N—O—CO-alkyl, NO—$(R_a)_{n1}$-Het, N—O—$(Y)_{n1}$—N $R_a$ $R_b$, N—O—CO—N($R_b$ $R_c$), radical with Het representing an aliphatic nitrogeneous heterocycle, Y being an optionally substituted —$CH_2$— radical, n1 being 1 to 3, and X is an halogen atom selected in the group comprising F, Cl, Br, I, and Z is H or $CH_3$ and the salts thereof.

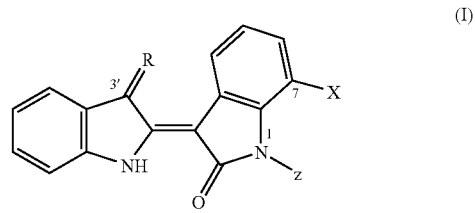

(I)

16 Claims, 17 Drawing Sheets

Figure 1:
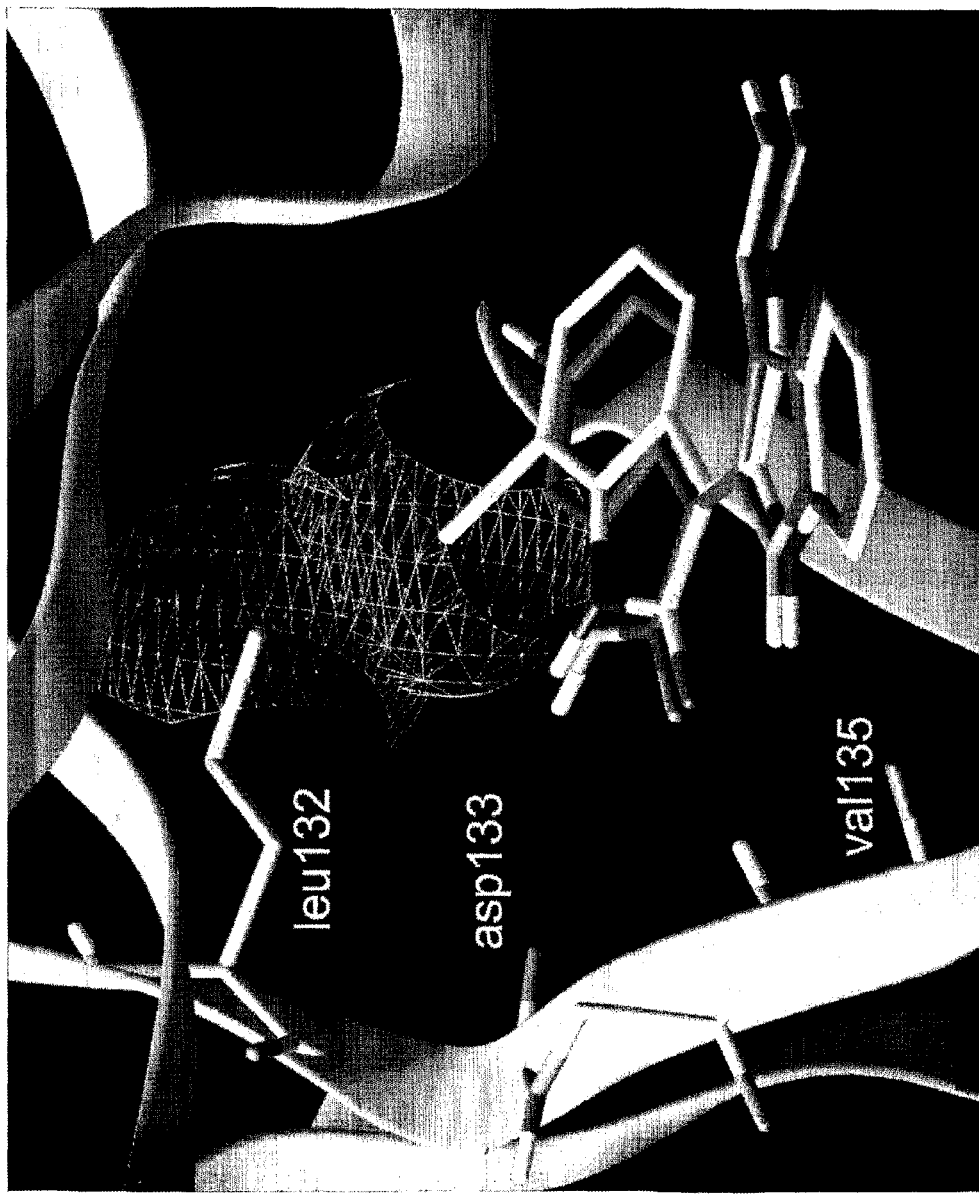

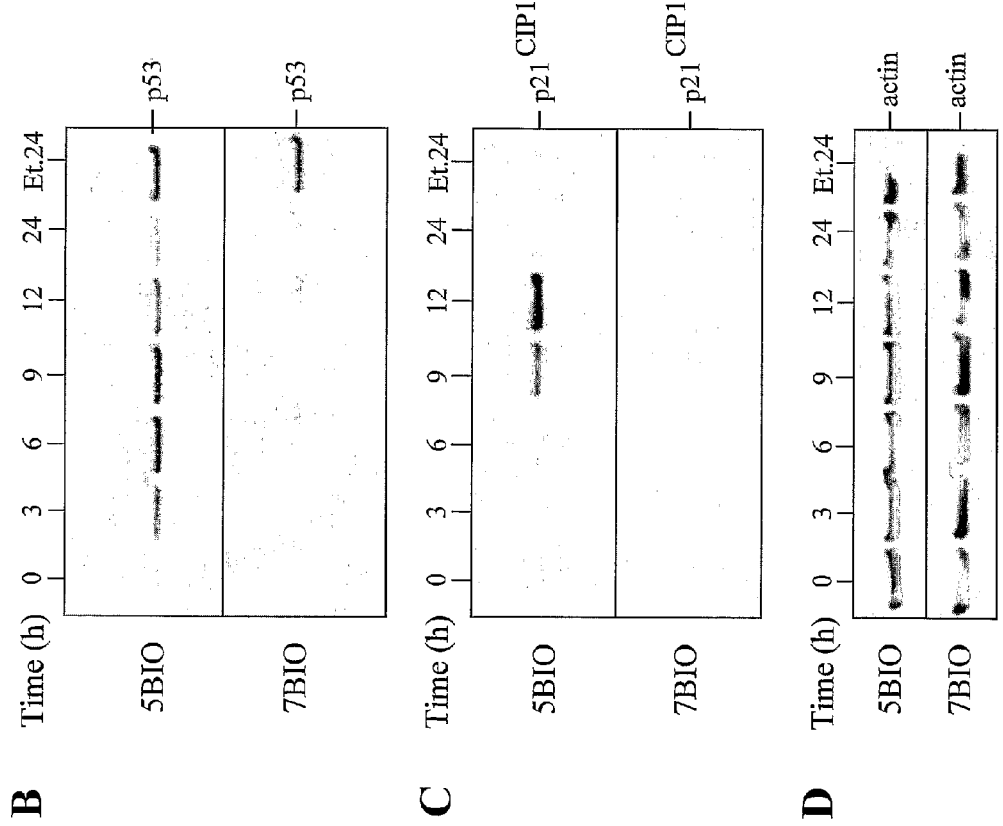
Figure 12B-D

7-SUBSTITUTED INDIRUBIN-3'OXIMES AND THEIR APPLICATIONS

This application is the U.S. national phase of International Application No. PCT/IB2006/004152, filed 21 Dec. 2006, which designated the U.S. and claims priority to U.S. Provisional Application Nos. 60/752,874 filed 23 Dec. 2005 and 60/785,377 filed 24 Mar. 2006, the entire contents of each of which are hereby incorporated by reference.

The invention relates to new 3'-, 7-substituted indirubins and their applications, particularly as anti-tumor agents.

Indirubin can be extracted from four different natural sources: indigo-producing plants, Tyrean purple-producing mollusks, various recombinant bacterial strains, and urine from various mammals including man (reviews in Meijer et al., 2006). Indirubin has been reported as the active ingredient of a traditional Chinese medicinal recipe, Danggui Longhui Wan, used to treat several diseases such as chronic myelocytic leukemia.

Interest in indirubin and derived analogues (collectively referred to as indirubins) strongly increased when they were discovered to inhibit cyclin-dependent kinases (CDKs), glycogen synthase kinase-3 (GSK-3), glycogen phosphorylase b and to bind and activate the Aryl Hydrocarbon Receptor (AhR), known also as the dioxin receptor.

Indirubins have been co-crystallized with CDK2, CDK2/cyclin A, CDK5/p25, PfPK5, the *Plasmodium falciparum* CDK1 homolog, GSK-3β, and glycogen phosphorylase b.

Indirubins display clear anti-proliferative and cell death-inducing effects. Although there is evidence suggesting that these effects originate from inhibition of CDKs, interaction with AhR, and subsequent induction of $p27^{kip1}$, may also contribute to the cellular effects of indirubins.

Furthermore some indirubins have recently been shown to prevent the activity of the transcription factor STAT3, probably by inhibition of its src-dependent tyrosine phosphorylation. This leads to down-regulation of survival factors such as survivin and Mcl-1, followed by cell death induction.

The inventors have found that 3'-, 7-substituted indirubins, despite weak or insignificant inhibitory activity on various classical kinase targets of indirubins, surprisingly induce cell death in a diversity of human tumors.

An object of the invention is then to provide new indirubins 3'-, 7-, substituted indirubins.

Another object of the invention is to provide a process for the synthesis of such indirubin derivatives, especially water-soluble indirubins.

Still another object is to provide pharmaceutical compositions containing said indirubine derivatives, particularly useful for treating a diversity of tumors.

This is also another object to provide a method of treatment of tumors by using such derivatives.

The invention more specifically relates to 3'-, 7-substituted-indirubins of formula (I)

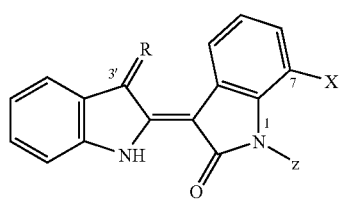

(I)

wherein R represents N—OH, N—O-alkyl or N—O—CO-alkyl, NO—$(R_a)_{n1}$-Het, N—O—$(Y)_{n1}$—N $R_a$ $R_b$, N—O—CO—N($R_b$, $R_c$), radical with Het representing an aliphatic nitrogeneous heterocycle, Y being an optionally substituted —$CH_2$— radical, n1 being 1 to 3, and X is an halogen atom selected in the group comprising F, Cl, Br, I, and Z is H or $CH_3$ and the salts thereof.

Surprisingly, said indirubins induce cell death via different mechanisms.

Indeed, these indirubin derivatives display potent cell death inducing properties in a diversity of human tumors acting through caspase-dependent and/or caspase-independent mechanisms.

In a first family, inducing cell death in a caspase-independent way, R more particularly represents OH.

In a second family, exhibiting a mixed caspase-dependent and caspase-independent mechanism of action, R represents a N—O-alkyl radical, particularly a N—O—C1-C3 alkyl radical and more preferably a N—O—$CH_3$ radical.

In a third family, the indirubins act mostly through a classical, caspase-dependent mechanism. In this family, R represents substitutions and their salts such as NO—$(R_a)_{n1}$-Het, N—O—$(Y)_{n1}$—N $R_a$ $R_b$, N—O—CO—N($R_b$, $R_c$) with $R_a$, n1, Het, $R_b$ et $R_c$ as above defined. Particularly R is A, As, B, Bs, C, Cs, D, Ds, E, Es, G, Gs, F or H such as defined in Table 2.

In preferred derivatives of said families, X represents Br and Z is H.

The invention also relates to a process for making 7-substituted indirubin derivatives as described below.

The synthesis of 7-halogeno-indirubins was mainly based on the dimerization reaction of an appropriately substituted isatin derivative with 3-acetoxyindole, as depicted in Scheme 1.

The desired isatins were synthesized through a two step procedure, using the corresponding commercial 7-halogeno-anilines Ia-d as starting material.

In the first step, the appropriate aniline derivatives were reacted with chloral hydrate and hydroxylamine hydrochloride to give the corresponding isonitrosoacetanilides IIa-d.

In the second step, the intermediate isonitrosoacenilides were heated under acidic conditions, particularly in concentrated sulfuric acid, to give the 7-halogeno-isatines (IIIc-d).

7-Halogeno-N-methylisatines (IVa-d) were prepared from respectively, by treatment with dimethyl sulfate and $Na_2CO_3$.

The substituted isatins, 7-halogeno-isatines (IIIc-d) or 7-halogeno-N-methylisatines (IVa d) were reacted with 3-acetoxyindole in alkaline medium to give, generally in a good yields, the corresponding bis-indoles selectively in a Z form (see derivatives 7, 15, 23, 31, 11, 19, 27 and 35 in the examples).

The oximes (see derivatives 8, 16, 24, 32, 12, 20, 28, and 36 in the examples) were prepared selectively in a (2'Z,3'E) form following a typical procedure from the appropriate indirubin derivatives (derivatives 7, 15, 23, 31, 11, 19, 27, and 35 in the examples) with hydroxylamine hydrochloride in an organic solvent such as pyridine under reflux.

A similar typical procedure was followed for the preparation of the methoximes (derivatives 9, 17, 25, 33, 13, 21, 29, and 37 in the examples) using methoxylamine hydrochloride.

The acetoximes (such as derivatives 10, 18, 26, 34, 14, 22, 30, and 38 in the examples) were prepared from the oximes with acetic anhydride in an organic solvent such as pyridine. The temperature of the reaction was carefully kept at 0° C. to avoid bisacetylation.

The synthesis of the 3'-substituted oximes of 7BIO and Me7BIO was based on the reaction of the 3'-[O-(2-bromoethyl)oxime] intermediates (such as 57 or 58 in the examples) with the appropriate amine: pyrrolidine, morpholine, piperazine, imidazol, dimethylamine and diethylamine.

Said intermediates 57 and 58 were prepared by the reaction of 7BIO or Me7BIO with 1,2-dibromoethane in DMF and Et₃N at room temperature.

In addition, carbamates (such as 63 and 64 in the examples) were prepared by the reaction of 7BIO or Me7BIO or analogs with N,N-diethylcarbamyl chloride.

Suitable reagents and conditions in steps a-j are as follows:

(a) chloral hydrate, $Na_2SO_4$, $H_2NOH \cdot HCl$, $H_2O$, $H^+$; (b) $H_2SO_4$, (c) $(CH_3)_2SO_4$, $Na_2CO_3$, DMF; (d) 3-acetoxyindole, $Na_2CO_3$/MeOH 25° C.; (e) $H_2NOCH_3$; hcL, Py, 120° C.; (f) $H_2NOCH_3 \cdot HCl$, Py, 120°; (g) $Ac_2O$, Py, 0° C.; (h) dibromoethane, triethylamine, DMF an, 25° C.; (i) DMF an, 25° C., amine (j) N,N-diethylcarbamyl chloride, triethylamine, DMF an, 25° C.

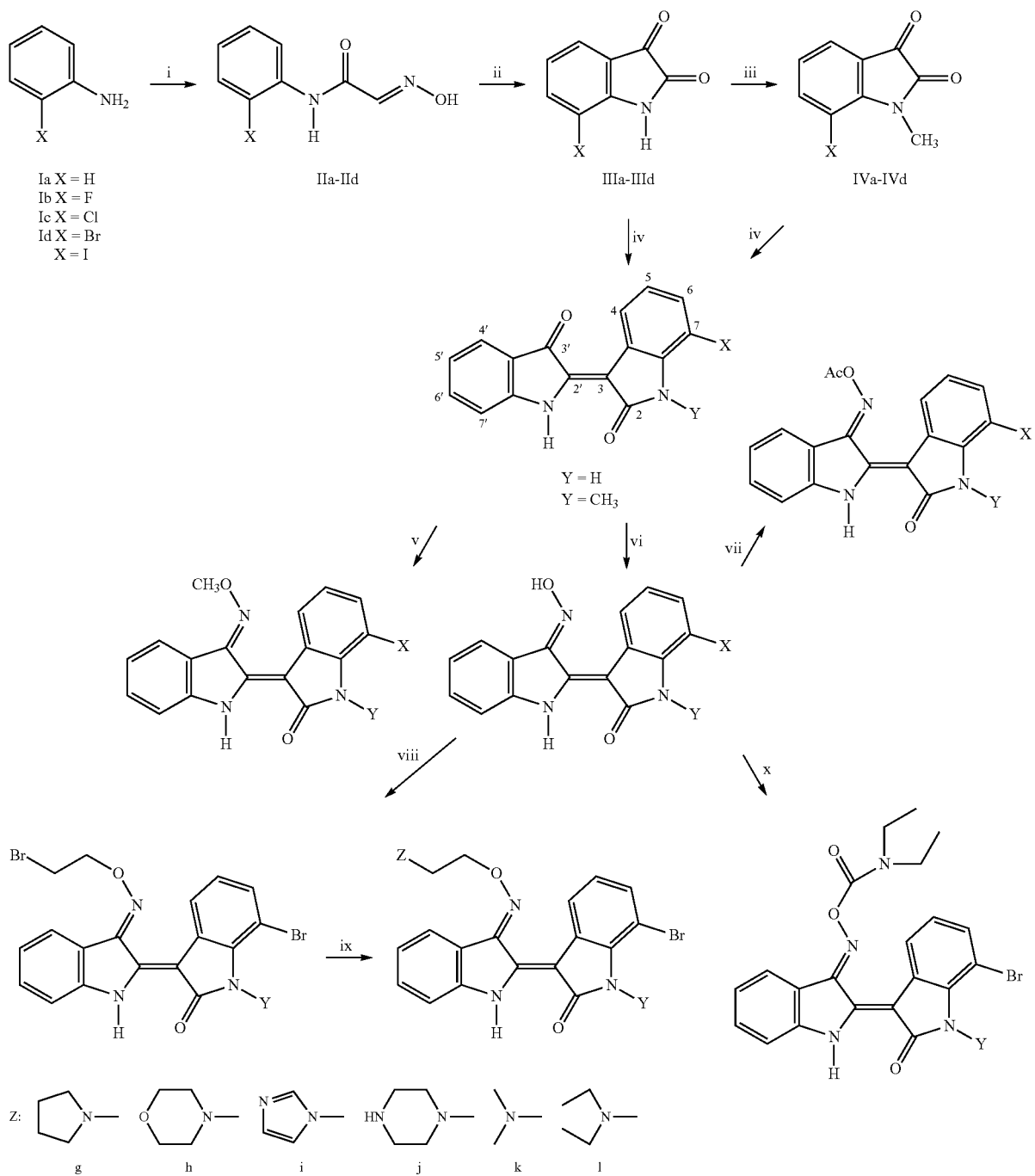

Scheme 1. General synthesis scheme of 3′,7-substituted indirubins.

As illustrated by the examples given hereinafter, the above disclosed 7-substituted indirubin-3'-oxime derivatives of the invention have valuable biological properties. Their effects on neuroblastoma cell survival and on human tumor cell lines are particularly advantageous and are confirmed in vivo, demonstrating their high interest as anti-tumor agents. Moreover, they have a high inocuity.

Said derivatives are then particularly suitable as active principle of drugs.

The invention thus also relates to pharmaceutical compositions comprising an effective amount of at least a 3'-, 7-substituted indirubin derivative such as above defined, in combination with a pharmaceutically acceptable carrier.

Said pharmaceutical compositions are formulated to be administered under oral, injectable, parental routes, with individual doses appropriate for the patient to be treated.

Said compositions are particularly useful to treat human tumors which have developed apoptosis resistance mechanisms. They are especially efficient for treating colon breast, lung, prostate cancers, neuroblastoma, hepatoma or leukemia.

The invention also relates to a method of treatment of human tumors which have developed apoptosis resistance mechanisms, comprising administering to the patient in need thereof an efficient amount of a composition such as above defined.

Other characteristics and advantages of the invention are given hereafter with reference to FIGS. 1 to 15, which represent, respectively:

FIG. 1: Superimposition of 7BIO (turquoise) and 6BIO (red) docked into the active site of GSK-3β. Only the backbone atoms of the residues from Asp133 to Val135 interacting with the ligands are visible while the rest of the protein ois presented as a ribbon. In the case of 7BIO a steric clash between the bromine atom at position 7 and the Leu132 residue occurs (visualized by overlap of the VdW spheres) resulting in a lower affinity of 7BIO for GSK-3β

Figure 2:
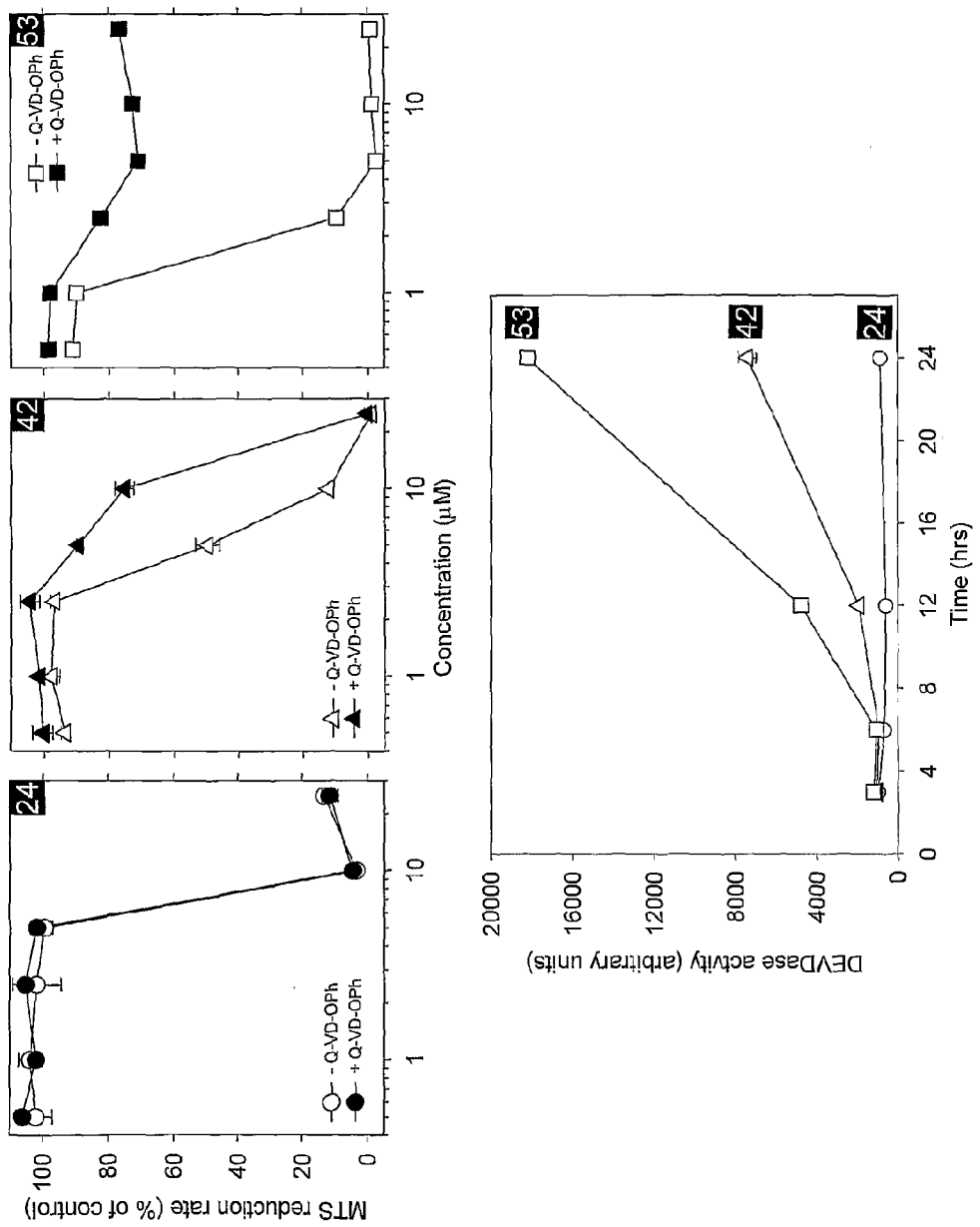

FIG. 2: 7-bromo-indirubins induce caspase-independent or caspase-dependent cell death. (Upper panel) SH-SY5Y cells were exposed for 48 h to increasing concentrations of three 7-bromo-indirubins (24, 42, 53) in the presence (filled symbols) or absence (open symbols) of 20 μM Q-VD-OPh. Cell survival was assessed by the MTS assay and is expressed as a percentage of untreated cells. Every point is the mean±s.e. of two independent experiments with two independent measurements per experiment. (B). The time-course of effector caspase activity was determined in SH-SY5Y cells treated with 25 μM of three 7-bromo-indirubins (24, 42, 53) for 24 h. DEVDase activity was measured as arbitrary fluorescence units. Every point is the mean±s.e. of three independent determinations.

Figure 3:
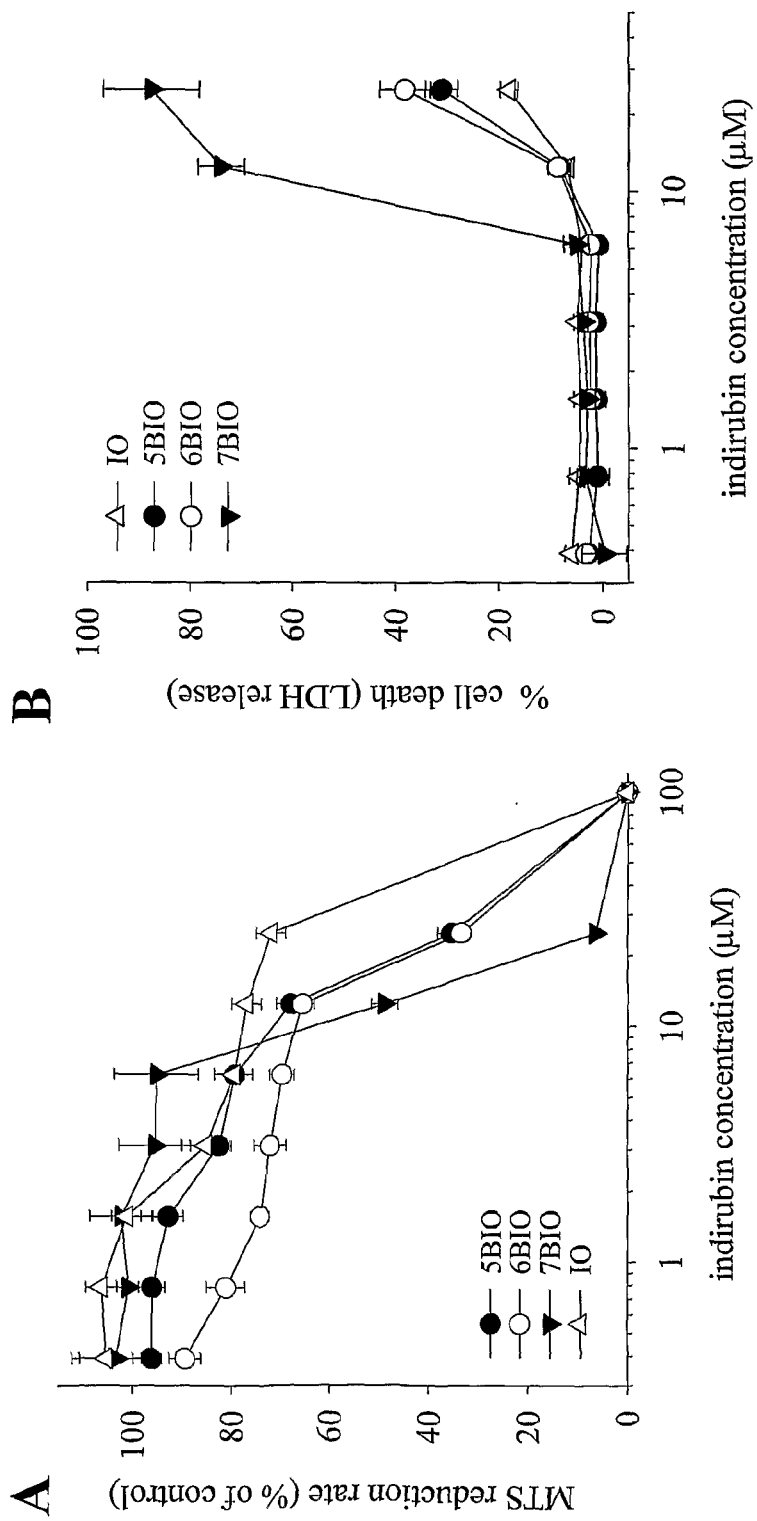
Figure 4:
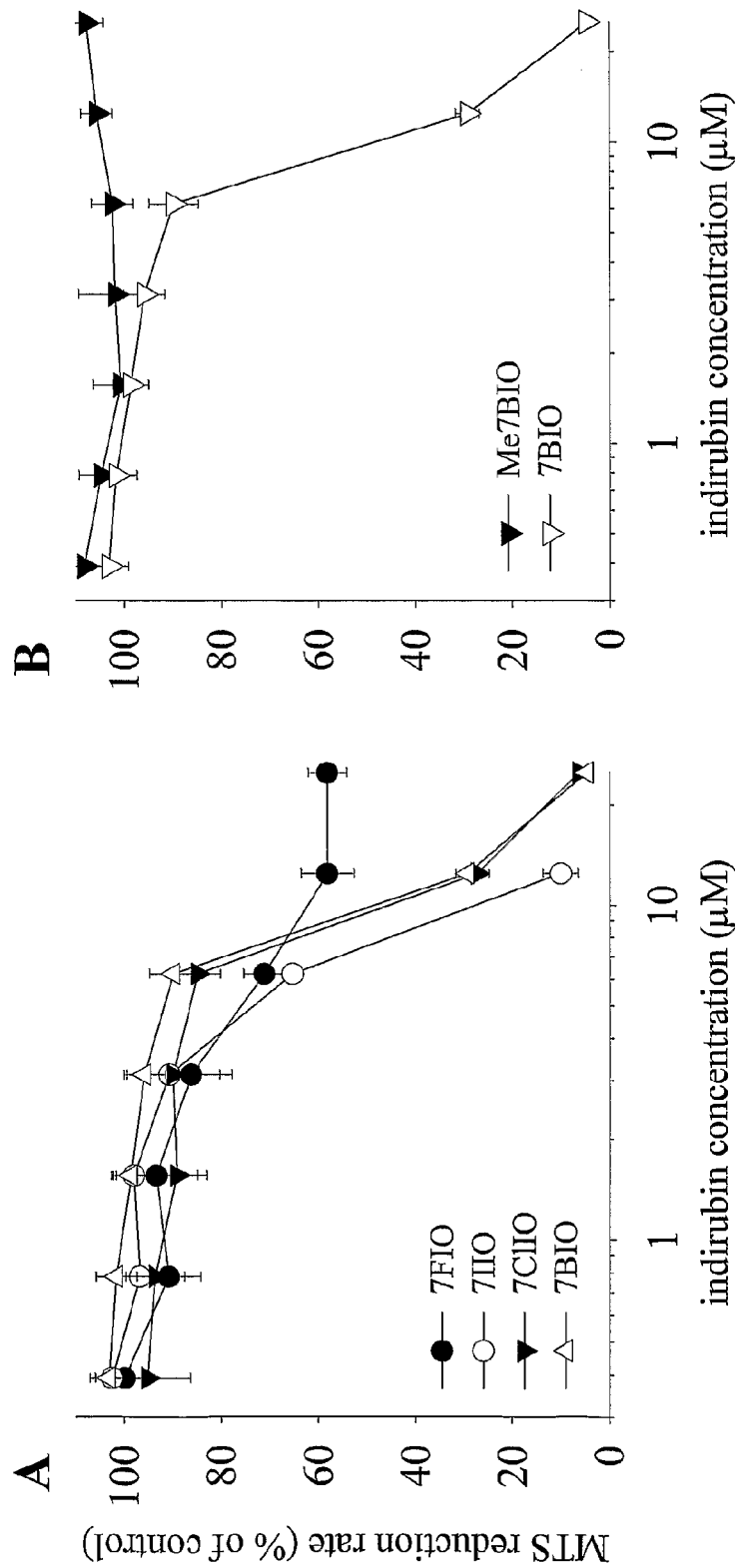
Figure 5:
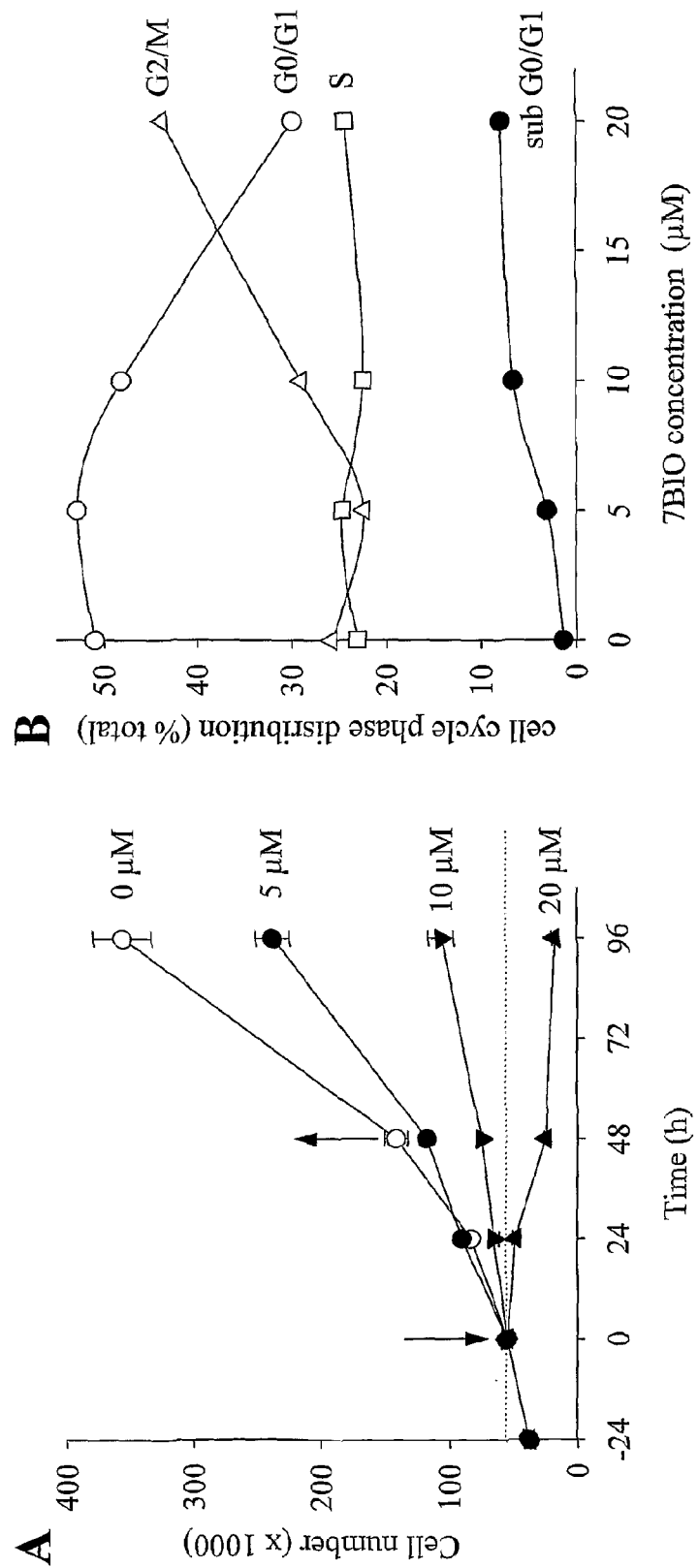
Figure 6:
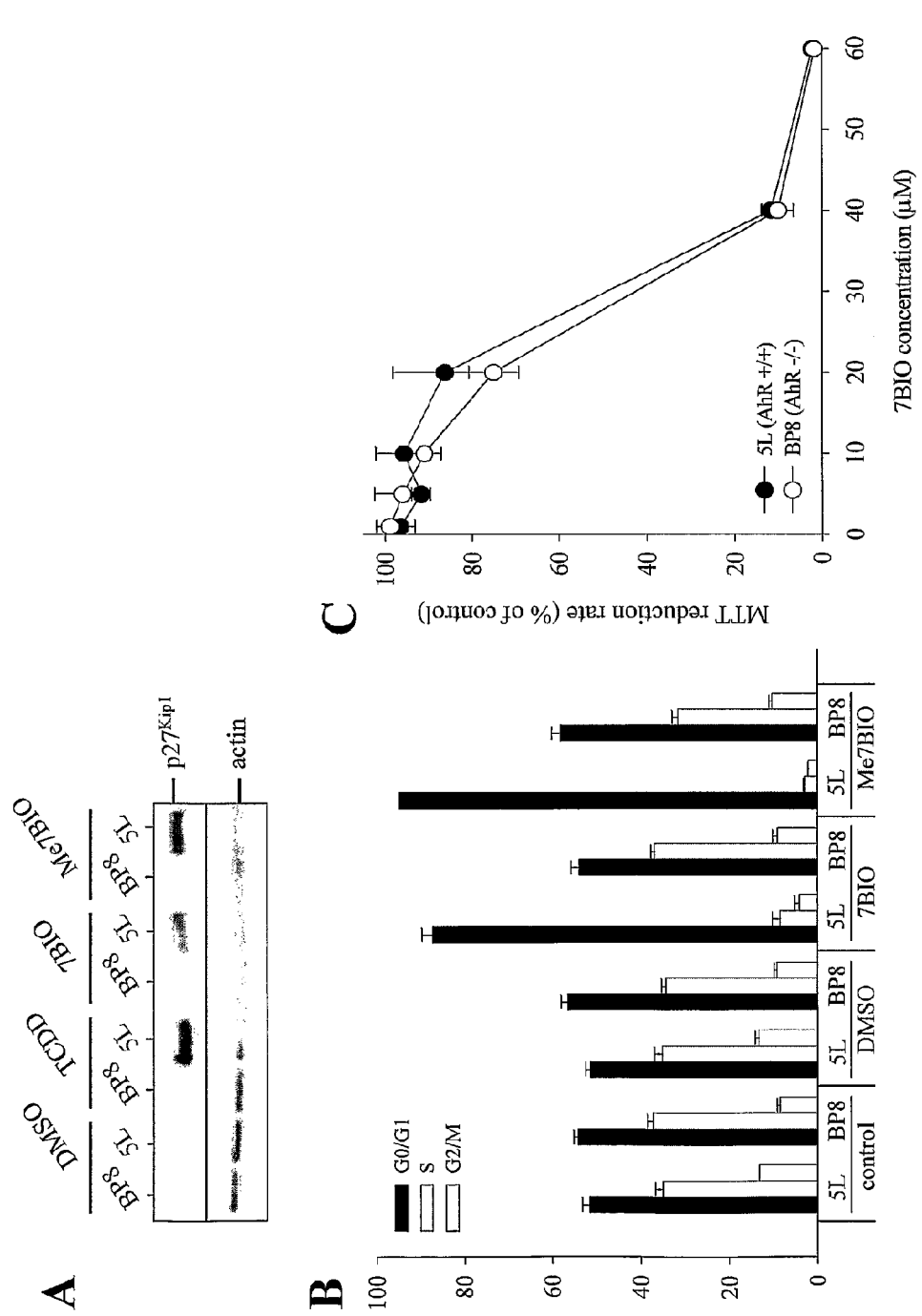

FIG. 3: the effects of IO, 5BIO, 6BIO and 7BIO on the survival of SH-SY5Y cells. (A) SH-SY5Y cells were exposed for 48 h to increasing concentrations of IO, 5BIO, 6BIO or 7BIO. Cell survival was estimated by the MTS reduction assay and is expressed in % of survival in untreated cells. Average±s.e. of at least four independent experiments with three independent measurements per experiment. (B) A similar experience was performed but LDH release was BIO dose-response curves were perfomed with the MTS reduction assay in the presence of 1 or 10% FCS;

FIG. 4: the effects of various 7-halogeno-indirubin-3' oxime (A) and 1-methyl-7-bromo-indirubin-3' oxime (B) on the survival of SH-SY5Y cells. SH-SY5Y cells were exposed for 48 h to increasing concentrations of 7-chloro-, 7-iodo-, 7-bromo-, or 7-fluoro-indirubin-3' oximes (7CIO, 7IIO, 7BIO, 7FIO, respectively) (A) or 1-methyl-7-bromo-indirubin-3' oxime (Me7BIO) or 7BIO (B). Cell survival was estimated by the MTS reduction assay and is expressed in % of survival in untreated cells. Average±s.e. of three determinations;

FIG. 5: the effects of 7BIO on cell proliferation and cell cycle distribution in MDA-MB-231 cells. (A) Cells were exposed at time 0 to various concentrations of 7BIO and cell numbers were determined at various times. At 48 h, the culture medium was replaced by fresh medium devoid of 7BIO. (B) Cells were exposed to various concentrations of 7BIO for 24 h and their distribution in the various cell cycle phases was determined by FACS analysis;

FIG. 6: the cytotoxic effect of 7BIO is independent of AhR. (A) Hepatocyte AhR−/− (BP8) and AhR+/+ (5 L) cells were treated with 0.1 μM TCDD, or 10 μM 7BIO or Me7BIO for 24 h or with the vehicle DMSO. The expression level of p27$^{KIP1}$ was determined by Western blotting using a specific antibody. Actin Western blotting was used as a loading control. (B) Both 7BIO and Me7BIO induce an Ah-dependent accumulation in G0/G1. 5 L and BPS cells were cultured in the absence (control) or presence of DMSO or 10 μM 7BIO or Me7BIO for 24 h, and the cell cycle phase distribution was determined by FACS analysis. (C) Both 5 L and BP8 cell lines were exposed for 24 h to increasing concentrations of 7BIO or Me7BIO. Cell survival was estimated by the MTT reduction assay and is expressed in % of survival in untreated cells. Average±s.e. of three determinations.

Figure 7:
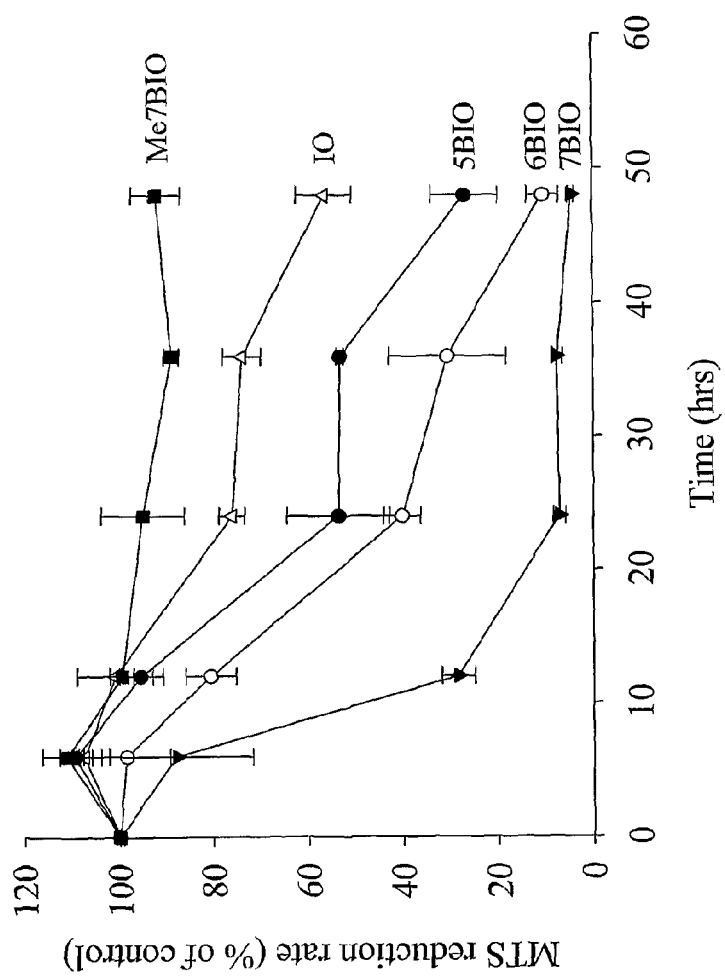

FIG. 7: 7BIO induces cell death much faster than other indirubins. SH-SY5Y cells were treated with 25 μM IO, 5BIO, 6BIO, 7BIO or Me7BIO for 6, 12, 24, 36 or 48 h. Cell survival was assessed by the MTS procedure. Every point is the mean±s.e. of two independent experiments with at least three independent measurements per experiment.

Figure 8:
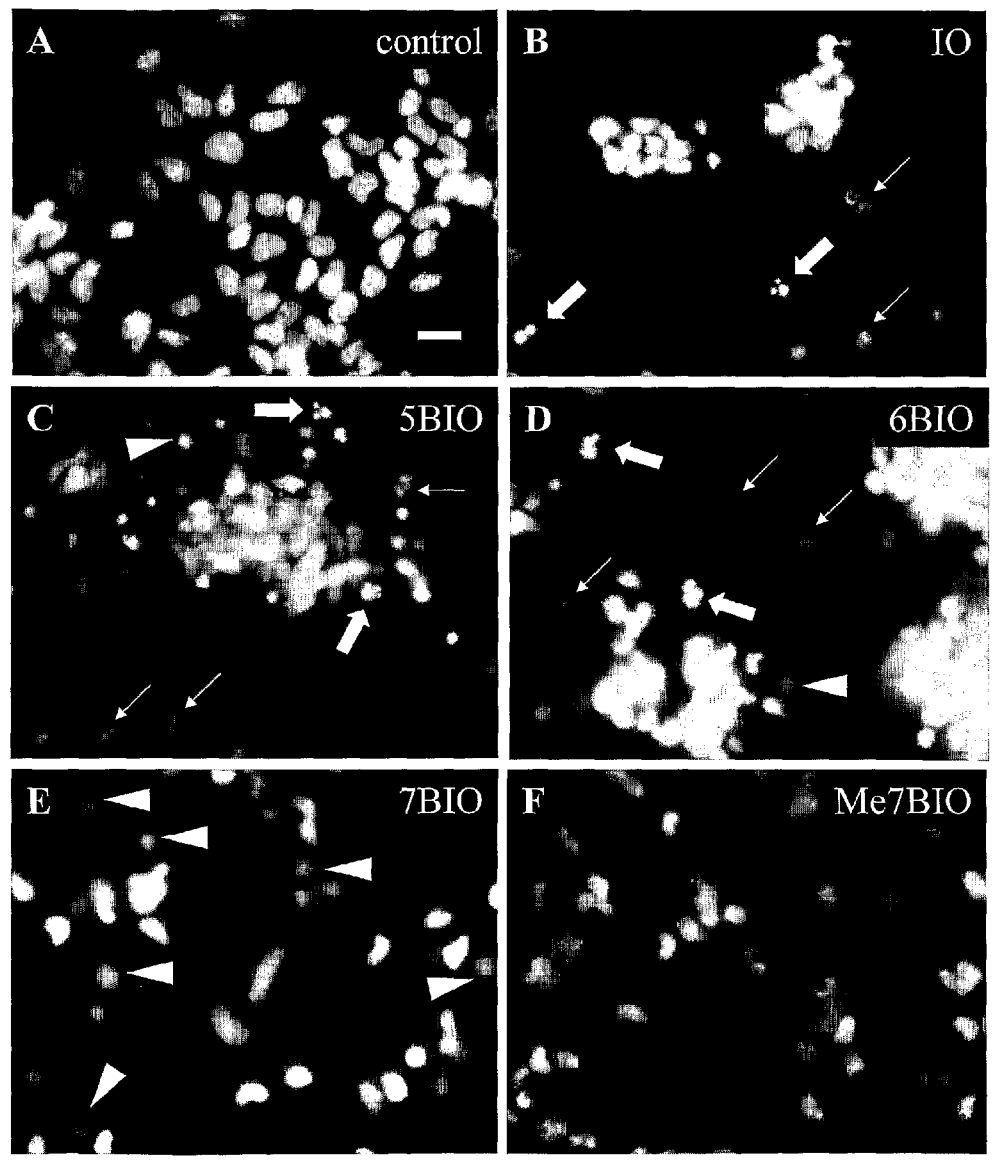

FIG. 8: in contrast to IO, 5BIO and 6BIO, 7BIO induces non-apoptotic cell death in SH-SY5Y cells. SH-SY5Y cells were exposed for 24 h to 0.1% DMSO (control) (A), 25 μM IO (B), 25 μM 5BIO (C), 10 μM 6BIO (D), 10 μM 7BIO (E) or 10 μM Me7BIO (F). Following double staining of DNA with BisBenzimide and propidium iodide, cells were examined by fluorescence microscopy. Thick arrows: apoptosis (nuclear fragmentation); thin arrows: secondary necrosis; arrow heads: pycnotic nuclei. Scale bar: 20 μm.

Figure 9:
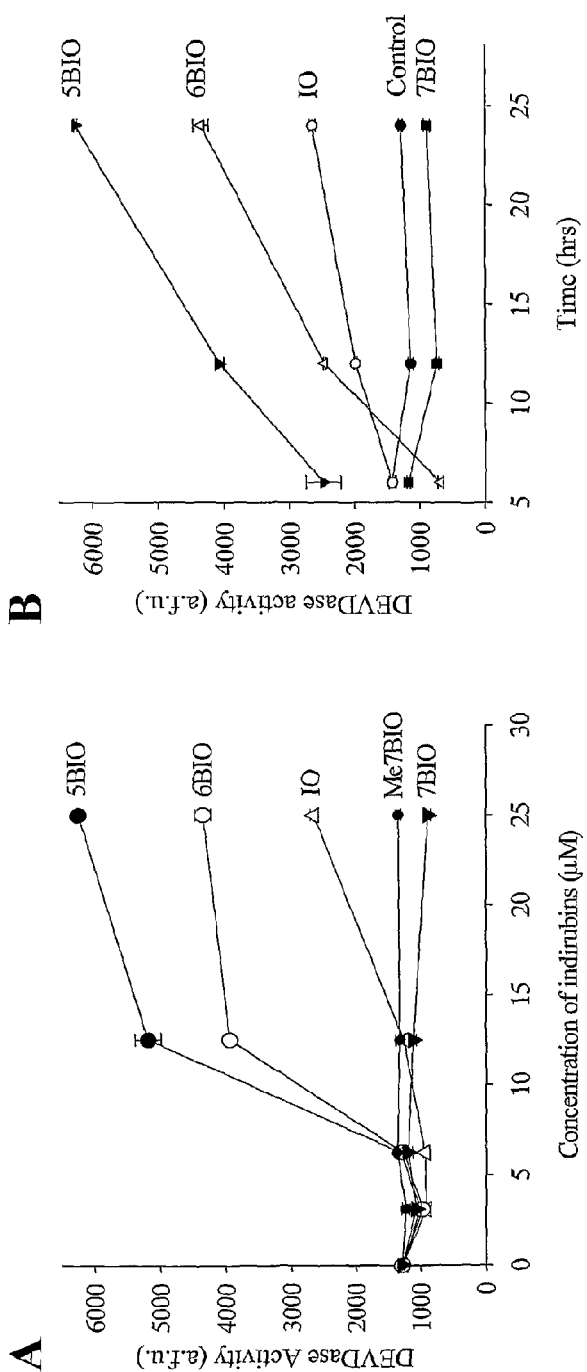

FIG. 9: 7BIO does not induce caspase activation. (A) SH-SY5Y cells were treated with IO, 5BIO, 6BIO, 7BIO or Me7BIO for 24 h in the range of concentrations shown. The value of control untreated cells is placed at time 0. DEVDase activity was measured as arbitrary fluorescence units. Every point is the mean±s.e. of at least three independent determinations. (B). The time course of effector caspase activity was determined in SH-SY5Y cells treated with 25 μM IO, 5BIO, 6BIO, 7BIO or Me7BIO for 24 h. Every point is the mean±s.e. of at least three independent determinations.

Figure 10:
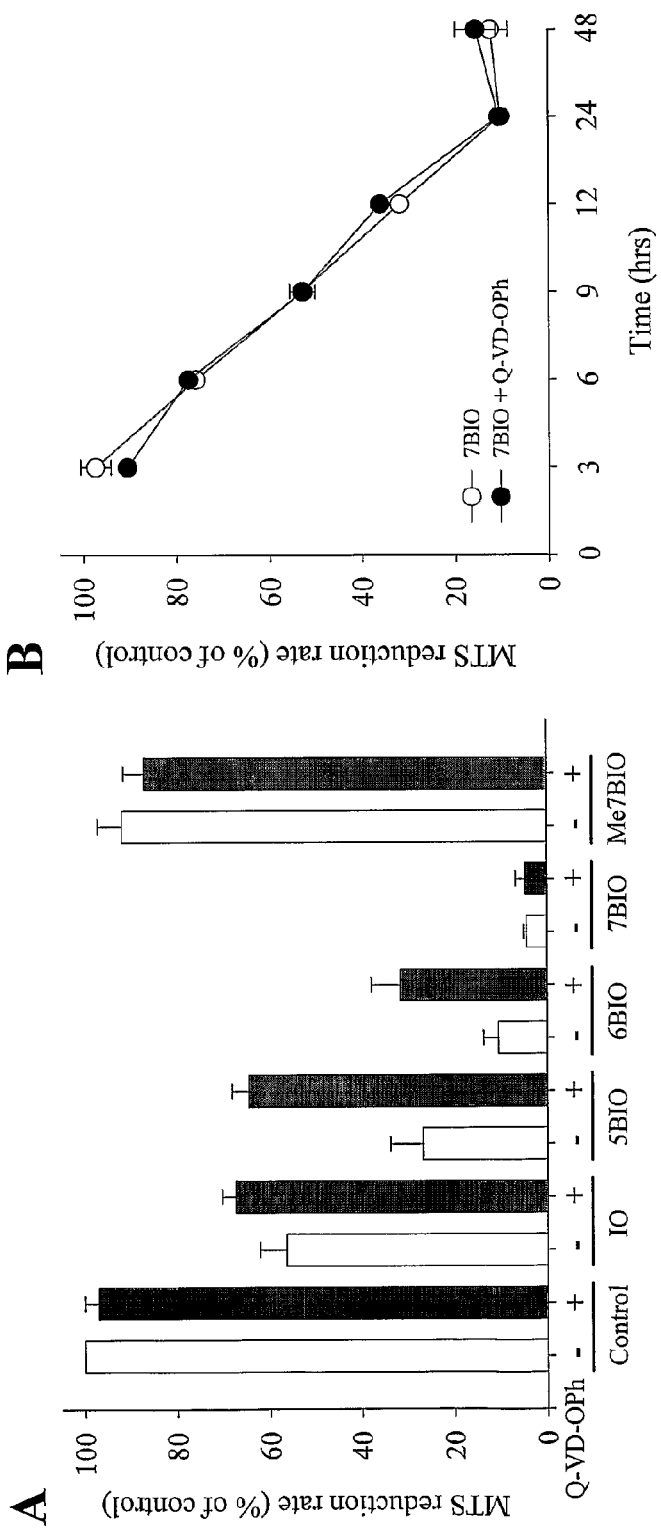

FIG. 10: 7BIO-induced cell death is not prevented by Q-VD-OPh, a general caspase inhibitor. (A) SH-SY5Y cells were treated with 25 μM IO, 5BIO, 6BIO, 7BIO or Me7BIO for 48 h in the presence (black bars) or absence (white bars) of 10 μM Q-VD-OPh, a broad spectrum inhibitor of caspases. Cell survival was assessed by the MTS assay. Every point is the mean±s.e. of four independent experiments with three independent measurements per experiment. In the control Q-VD-OPh graph only two independent experiments were performed. (B) Time-course of 7BIO-induced cell death in the absence (○) or presence (●) of 10 μM Q-VD-OPh. Cells were exposed to 25 μM BIO at time 0 and cell survival was estimated at different time-points by the MTS assay. Each point is the mean±s.e. of at least three independent experiments with three independent measurements per experiment.

Figure 11:
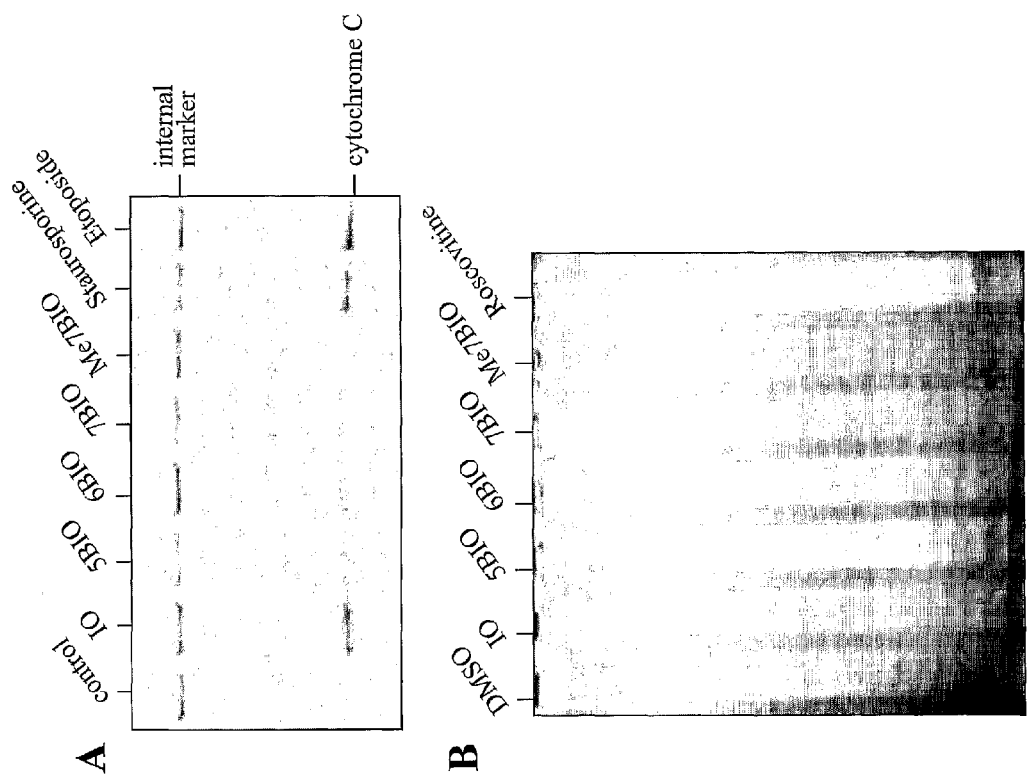

FIG. 11: IO, 5BIO and 6BIO, but not 7BIO, induce cytochome C release and DNA laddering. (A) SH-SY5Y cells were treated with 12.5 µM IO, 5BIO, 6BIO, 7BIO or Me7BIO, 0.25 µM staurosporine or 12.5 µM etoposide for 10 h. Cells were then harvested and fractionated into a nuclear pellet and a cytoplasmic supernatant. The latter was resolved by SDS-PAGE followed by Western blotting using an anti-cytochome C antibody. The antibody cross-reacts with an irrelevant protein used as an internal loading marker. (B) SH-SY5Y cells were treated with DMSO (0.25%), 25 µM IO, 5BIO, 6BIO, 7BIO or Me7BIO, or 25 µM (R)-roscovitine for 24 h. Cells were then harvested and internucleosomal DNA fragmentation was analyzed by electrophoresis in 1.5% agarose gels.

FIG. 12: 7BIO does not induce nor require p53 nor $p21^{CIP1}$ expression. (A) SH-SY5Y cells were treated with 12.5 µM IO, 5BIO, 6BIO, 7BIO or Me7BIO, 1 µM staurosporine or 12.5 µM etoposide for 12 h. Cells were then harvested and proteins were resolved by SDS-PAGE followed by Western blotting using antibodies directed against p53, $p21^{CIP1}$ or actin (used as internal loading marker). (B-D) SH-SY5Y cells were treated with 12.5 µM 5BIO or 7BIO or 12.5 µM etoposide for various times. Cells were then harvested and proteins were resolved by SDS-PAGE followed by Western blotting using antibodies directed against p53 (B), $p21^{CIP1}$ (C) or actin (D). (E) wild-type (●) and p53-deprived (○) HCT-116 cells were exposed for 24 h to increasing concentrations of 7BIO or Me7BIO. Cell survival was estimated by the MTS reduction assay and is expressed in % of survival in untreated cells. Average±s.e. of three determinations.

Figure 13:
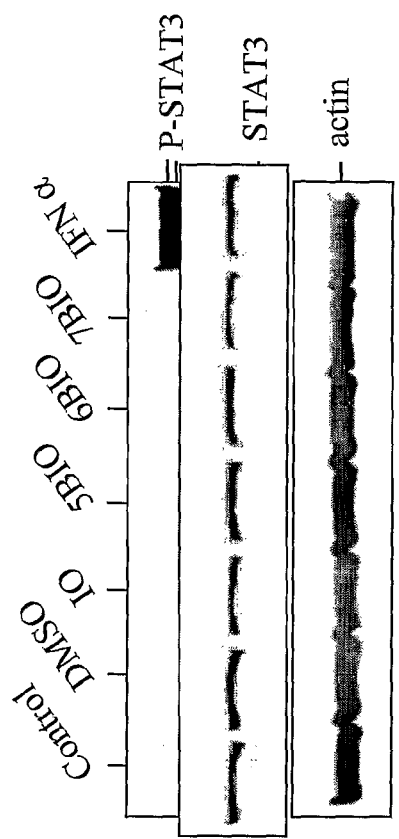

FIG. 13: 7BIO effects do not involve down-regulation of STAT3 tyrosine phosphorylation. MDA-MB-231 cells were either untreated or treated with 25 µM IO, 5BIO, 6BIO, 7BIO, or the DMSO carrier for 4 h, or with 100 ng/ml of IFN-α for 5 min. Cellular proteins were resolved by SOS-PAGE followed by Western blotting using antibodies directed total STAT3 and Tyrosine-phosphorylated STAT3. Western blotting with anti-actin antibodies provided a loading marker.

Figure 14:
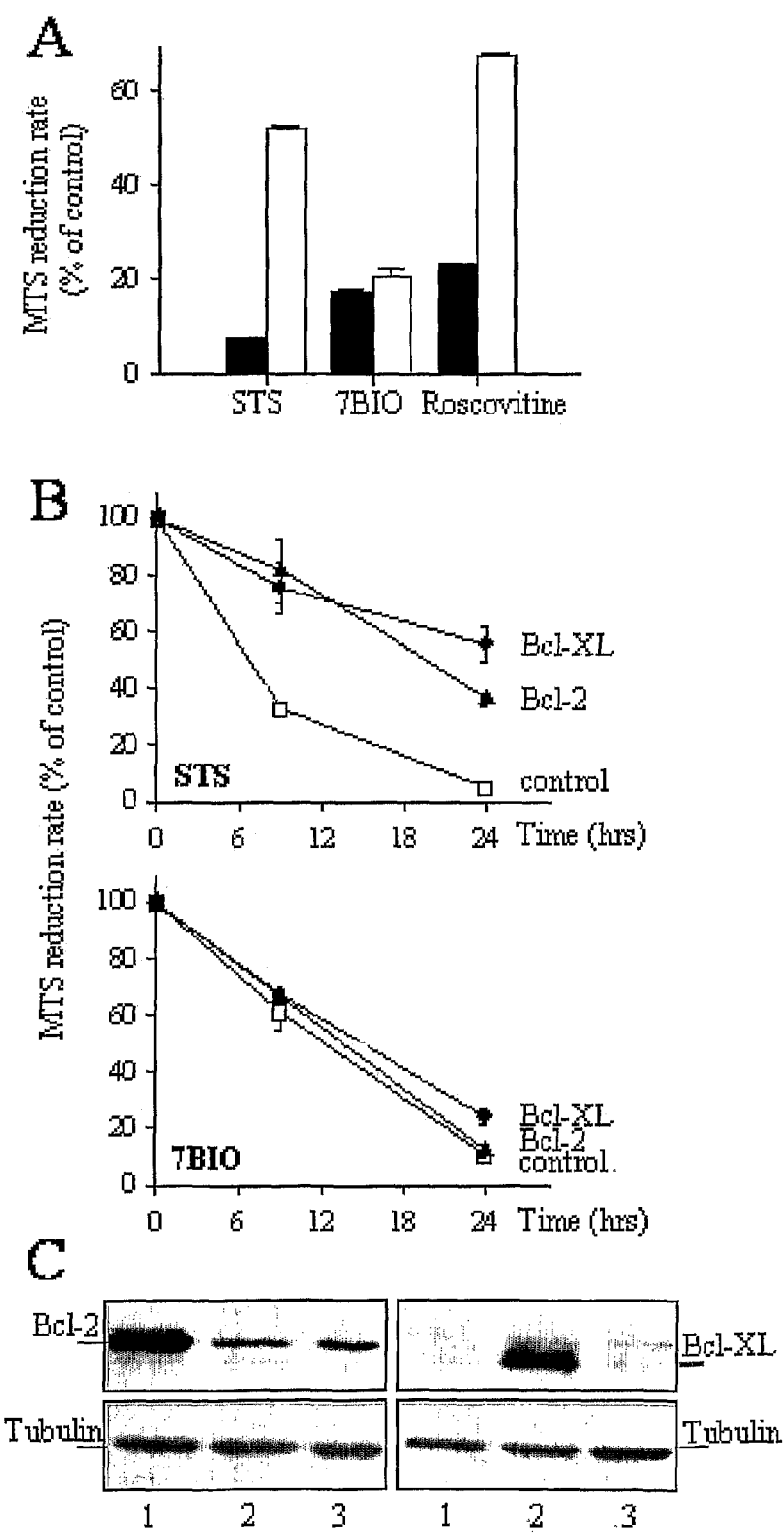

FIG. 14: In contrast to STS-induced apoptosis 7BIO-induced cell death is resistant to the protective effects of cell differentiation (A) or Bcl-2/Bcl-XL overexpression (B, C). (A) SH-SY5Y cells were either treated with RA during 5 days to induce quiescence and differentiation (white bars) or kept proliferating. (black bars). After 24 h of treatment with STS (1 µM), 7BIO (25 µM) or racemic Roscovitine (50 µM), cell viability was determined by the MTS procedure. Bar value is the mean±s.e. of at least 6 independent determinations. (B) SH-SY5Y cells, permanently transfected with the vectors pcDNA3/Bcl-XL (●), pcDNA3/Bcl-2 (○) and empty pcDNA3 (■), were treated with either STS (2 µM) or 7BIO (25 µM). Cell viability was analyzed by the MTS procedure at 9 and 24 h of treatment. In the time course plots, every point is the mean±s.e. of three independent experiments with six independent values per experiment. (C) The Bcl-XL and Bcl-2 content of pcDNA3/Bcl-2 (1), pcDNA3/Bcl-XL (2) and pcDNA3/empty (3) transfected SH-SY5Y cells was assessed during the viability determination experiments by Western blotting. Tubulin content was used to control for protein load.

Figure 15:
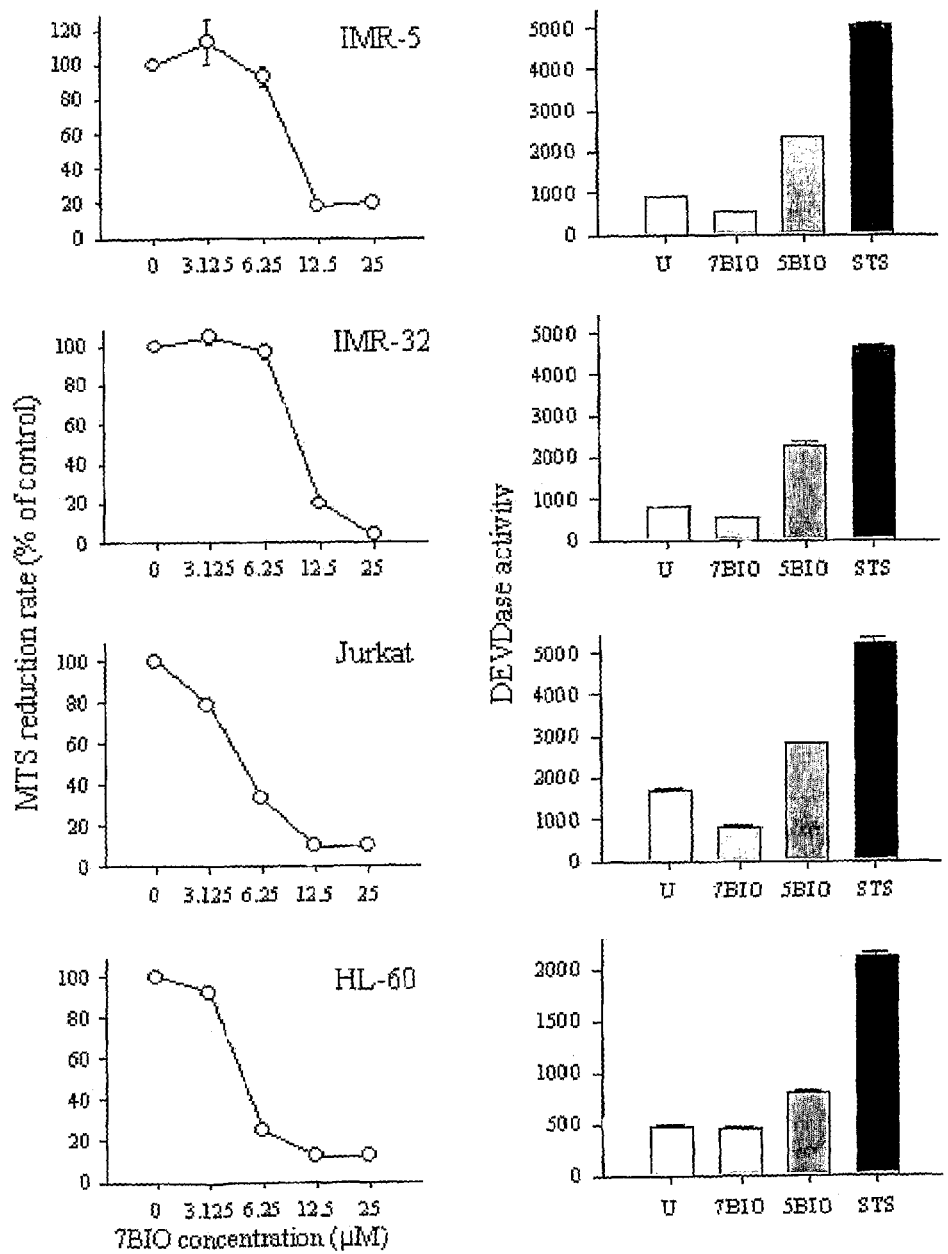

FIG. 15. 7BIO induces caspase-independent cell death in four additional cell lines. IMR-5, IMR-32, HL-60 and Jurkat cells were challenged with increasing concentrations of 7BIO for 24 h and cell viability was determined by the MTS procedure (left). Every point is the mean±s.e. of three independent experiments with six independent measurements per experiment. The same cell lines were subjected for 24 h to treatments with STS (1 µM), 5BIO (25 µM), 7BIO (25 µM) or left untreated (U) and the activation of effector caspases (DEVDase activity in arbitrary fluorescent units) was measured (right). Bar value is the mean±s.e. of 6 independent determinations.

MATERIAL & METHODS

Chemistry

General Chemistry Experimental Procedures

All chemicals were purchased from Aldrich Chemical Co. NMR spectra were recorded on Broker DRX 400; chemical shifts are expressed in ppm downfield from TMS. The $^1$H-$^1$H and the $^1$H-$^{13}$C NMR experiments were performed using standard Bruker microprograms. CI-MS spectra were determined on a Finnigan GCQ Plus ion-trap mass spectrometer using $CH_4$ as the CI ionization reagent. Column chomatographies were conducted using flash silica gel 60 Merck (40-63 µm), with an overpressure of 300 mbars. All the compounds gave satisfactory combustion analyses (C, H, N, within ±0.4% of calculated values).

Indirubin Synthesis General Procedures

5-Bromoindirubin (5BI), 7-bromoindirubin (7BI), 7-chloroindirubin (7CI), 7-iodoindirubin (7II), 7-fluoroindirubin (7FI) and 7-bromo-1-methylindirubin (Me7BI) were prepared from 5-bromoisatin, 7-bromoisatin, 7-chloroisatin, 7-iodoisatin, 7-fluoroisatin, 7-bromo-1-methylisatin, respectively, and 3-acetoxyindol.

5-Bromoindirubin-3'-oxime (5BIO), 7-bromoindirubin-3'-oxime (7BIO), 7-chloroindirubin-3'-oxime (7CIO), 7-iodoindirubin-3'-oxime (7IIO) 7-fluoroindirubin-3'-oxime (7FIO) and 1-methyl-7-bromoindirubin-3'-oxime (Me7BIO) were prepared from the corresponding indirubins and hydroxylamine hydrochloride. IO and 6BIO were synthesized as previously described (Leclerc et al, 2001; Polychonopoulos et al, 2004).

General Procedure for the Preparation of the Indirubin-Oximes 5BIO, 7BIO, 7CIO, 7IIO, 7FIO and Me7BIO The appropriate indirubin derivative 5BI, 7BI, 7CI, 7II, 7FI or Me7BI (1 mmol) was dissolved in pyridine (10 mL). With magnetic stirring, hydroxylamine hydrochloride (10 equiv) was added and the mixture was heated under reflux (120° C.) for 1.5 h. Then the solvent was evaporated under reduced pressure and the residue was washed with water and cyclohexane to afford quantitatively the corresponding 3'-oxime.

5-bromoindirubin-3'-oxime (5BIO)

$^1$H NMR (DMSO, 400 MHz, δ ppm, J σεHz) 13.70 (1H, s, NOH), 11.83 (1H, s, N'—H), 10.87 (1H, s, N—H), 8.76 (1H, d, J=2.1 Hz, H-4), 8.27 (1H, d, J=7.9 Hz, H-4'), 7.44 (2H, m, H-6', 7'), 7.28 (1H, dd, J=8.2, 2.0 Hz, H-6), 7.06 (1H, td, J=7.9, 2.0 Hz, H-5'), 6.85 (1H, d, J=8.2 Hz, H-7); CI-MS at/z 356, 358 (M+H)$^+$ 7-Bromoindirubin-3'-oxime (7BIO)

$^1$H NMR (DMSO, 400 MHz, δ ppm, J σε Hz) 13.68 (1H, brs, NOH) 11.90 (1H, s, N'—H), 10.91 (1H, s, N—H), 8.67 (1H, d, J=7.8 Hz, H-4), 8.23 (1H, d, J=7.8, H-4'), 7.42 (2H, m, H-6', 7'), 7.29 (1H, d, J=7.8 Hz, H-6), 7.06 (1H, t, J=7.8 Hz, H-5'), 6.90 (1H, t, J=7.8 Hz, H-5); CI-MS m/z/z 356, 358 (M+H)$^+$ 7-Chloroindirubin-3'-oxime (7CIO)

$^1$H NMR (DMSO, 400 MHz, δ ppm, J σε Hz) 13.70 (1H, brs, NOH) 11.86 (1H, s, N'—H), 11.09 (1H, s, N—H), 8.62

(1H, d, J=7.9 Hz, H-4), 8.23 (1H, d, J=7.6, H-4'), 7.44 (2H, m, H-6', 7'), 7.17 (1H, d, J=7.9 Hz, H-6), 7.06 (1H, t, J=7.6 Hz, H-5'), 6.96 (1H, t, J=7.8 Hz, H-5); CI-MS M/Z 312, 314 (M+H)$^+$

7-Iodoindirubin-3'-oxime (7IIO)

$^1$H NMR (DMSO, 400 MHz, δ ppm, J in Hz) 13.65 (1H, brs, NOH) 11.87 (1H, s, N'—H), 10.63 (1H, s, N—H), 8.68 (1H, d, J=7.8 Hz, H-4), 8.23 (1H, d, J=7.2, H-4'), 7.47 (1H, d, J=7.8 Hz, H-6), 7.43 (2H, m, H-6', 7'), 7.06 (1H, t, J=7.2 Hz, H-5'), 6.76 (1H, t, J=7.8 Hz, H-5); CI-MS m/z 404 (M+H)$^+$ 7-Fluoroindirubin-3'-oxime (7FIO)

$^1$H NMR (DMSO, 400 MHz, δ ppm, J σε Hz) 13.61 (1H, brs, NOH), 11.85 (1H, s, N'—H), 11.19 (1H, s, N—H), 8.44 (1H, d, J=7.8 Hz, H-4), 8.19 (1H, d, J=7.5, H-4'), 7.39 (2H, m, H-6', 7'), 7.00 (2H, m, H-5', 6), 6.90 (1H, m, H-5); CI-MS m/z 296 (M+H)$^+$ 1-Methyl-7-bromoindirubin-3'-oxime (Me7BIO)

$^1$H NMR (DMSO, 400 MHz, δ ppm, J σε Hz) 13.70 (1H, brs, NOH), 12.00 (1H, s, N'—H), 8.81 (1H, d, J=7.9 Hz, H-4), 8.23 (1H, d, J=7.9 Hz, H-4'), 7.43 (2H, m, H-6', 7'), 7.34 (1H, d, J=7.9 Hz, H-6), 7.07 (1H, t, J=7.9 Hz, H-5'), 6.93 (1H, t, J=7.9 Hz, H-5), 3.68 (3H, s, N—CH$_3$); CI-MS m/z 370, 372 (M+H)$^+$ General Procedure for the Preparation of Isatins IIIa-D and IVa-d Chloral hydrate (5.0 g) and Na$_2$SO$_4$ (35.0 g) were dissolved in water (70 mL) in a 300 mL beaker and warmed to 35° C. A warm solution of the appropriate commercial aniline derivative Ia-d (27.6 mmol) in water (20 mL) and aqueous solution of conc. HCl (3 mL) was added (a white precipitate of the amine sulfate was formed), followed by a warm solution of hydroxylamine hydrochloride (6.1 g) in water (27.5 mL). The mixture was stirred by hand and heated on a hot plate (a thick paste formed at 75-70° C.) at 80-90° C. for 2 h, then allowed to cool for 1 h, by which time the temperature had fallen to 50° C., and filtered. The pale cream product was washed by stirring with water (100 mL) and filtered. Drying overnight at 40° C. gave the corresponding isonitrosoacetanilide IIa-d.

Sulfuric acid (100 mL) was heated in a 3 L beaker on a hot plate to 60° C. and then removed. The dry isonitrosoacetanilide IIa-d was added in portion with stirring over 30 min so that the temperature did not exceed 65° C. The mixture was then heated to 80° C. for 15 min, allowed to cool to 70° C. and cooled on ice. The solution was poured on to crushed ice (500 mL) and left to stand for 1 h before filtering the orange-red precipitate. The product was washed by stirring with water (100 mL) and filtered to give the corresponding Isatins. Yields: IIIa: 57%, IIIb: 50%, IIIc: 65%, IIId: 50%.

7-Fluoro-N-methylisatin (IVa)

To a solution of IIIa (380 mg, 2.30 mmol) in dry acetone (60 mL) was added Na$_2$CO$_3$ (anh.) (3.5 g) and dimethylsulfate (0.4 mL) under Ar and the reaction mixture was heated at 60° C. for 20 h. Then, the mixture was filtered and the filtrate was carefully evaporated using a high vacuum pump (under 40° C.). The solid residue was submitted to flash chromatography with CH$_2$Cl$_2$ to afford IVa (288 mg, 1.61 mmol, 70%).

7-Chloro-N-methylisatin (IVb)

This compound was prepared from 7-chloroisatin (IIIb) by a procedure analogous to that of IVa: yield 76%.

7-Bromo-N-methylisatin (IVc)

This compound was prepared from 7-bromoisatin (IIIc) by a procedure analogous to that of IVa: yield 90%.

7-Iodo-N-methylisatin (IVd)

This compound was prepared from 7-iodoisatin (IIId) by a procedure analogous to that of IVa: yield 85%.

(2'Z)-7-Fluoroindirubin (7)

Methanol (25 mL) was vigorously stirred under nitrogen for 20 min and then 7-fluoroisatin (IIIa) (150 mg, 0.91 mmol) and 3-acetoxyindole (106 mg, 0.61 mmol) were added and stirring was Continued for 5 min. Anhydrous Na$_2$CO$_3$ (155 mg) was added and the stirring was continued for 3 h. The dark precipitate was filtered and washed with aqueous methanol (1:1, 20 mL) to give 7 (130 mg, 0.46 mmol, 77%) selectively in a Z form. $^1$H NMR (DMSO, 400 MHz, δ ppm, J in Hz) 11.37 (1H, s, N'—H), 11.12 (1H, s, N—H), 8.58 (1H, d, J=7.7 Hz, H-4), 7.64 (1H, d, J=7.5 Hz, H-4'), 7.57 (1H, t, J=7.5 Hz H-6'), 7.42 (1H, d, J=7.5 Hz, H-7'), 7.15 (1H, t, J=8.0 Hz, H-5), 7.02 (2H, m, H-5', 6); CI-MS m/z 281 (M+H)$^+$. Anal. (C$_{16}$H$_9$N$_2$O$_2$F) C, H, N.

(2'Z)-7-Chloroindirubin (15)

This compound was prepared from 7-chloroisatin (IIIb) by a procedure analogous to that of 7: yield 80%; $^1$H NMR (DMSO, 400 MHz, δ ppm, J in Hz) 11.29 (1H, s, N'—H), 11.16 (1H, s, N—H), 8.72 (1H, d, J=7.8 Hz, H-4), 7.66 (1H, d, J=7.5 Hz, H-4'), 7.59 (1H, t, J=7.8 Hz H-6'), 7.43 (1H, d, J=7.8 Hz, H-7'), 7.30 (1H, d, J=7.8 Hz, H-6), 7.05 (2H, m, H-5, 5'); CI-MS m/z 297, 299 (M+H)$^+$. Anal. (C$_{16}$H$_9$N$_2$O$_2$Cl) C, H, N.

(2'Z)-7-Bromoindirubin (23)

This compound was prepared from 7-bromoisatin (IIIc) by a procedure analogous to that of 7: yield 85%; $^1$H NMR (DMSO, 400 MHz, δ ppm, J in Hz) 11.18 (2H, br s, N—H), 8.77 (1H, d, J=7.9 Hz, H-4), 7.67 (1H, 7.5 Hz, H-4'), 7.59 (1H, t, J=7.5 Hz, H-6'), 7.44 (1H, d, J=7.9 Hz, H-6), 7.43 (1H, d, J=7.5 Hz, H-7'), 7.04 (1H, t, J=7.5 Hz, H-5'), 6.98 (1H, t, J=7.9 Hz, H-5); CI-MS m/z 341, 343 (M+H)$^+$. Anal. (C$_{16}$H$_9$N$_2$O$_2$Br) C, H, N.

(2'Z)-7-Iodoindirubin (31)

This compound was prepared from 7-iodoisatin (IIId) by a procedure analogous to that of 7: yield 90%; $^1$H NMR (DMSO, 400 MHz, δ ppm, J in Hz) 8.77 (1H, d, J=7.5 Hz, H-4), 7.64 (1H, d, J=7.5 Hz, H-4'), 7.59 (2H, m, H-6, 6'), 7.41 (1H, d, J=7.5 Hz, H-7'), 7.04 (1H, t, J=7.5 Hz, H-5'), 6.84 (1H, t, J=7.5 Hz, H-5); CI-MS m/z 389 (M+H)$^+$. Anal. (C$_{16}$H$_9$N$_2$O$_2$I) C, H, N.

(2'Z)-7-Fluoro-1-methylindirubin (11)

This compound was prepared from 7-fluoro-N-methylisatin (IVa) and 3-acetoxyindole by a procedure analogous to that of 7: yield 78%; $^1$H NMR (DMSO, 400 MHz, δ ppm, J in Hz) 11.22 (1H, s, N'—H), 8.66 (1H, d, J=8.0 Hz, H-4), 7.67 (1H, d, J=7.7 Hz, H-4'), 7.60 (1H, t, J=7.7 Hz, H-6'), 7.44 (1H, d, J=7.4, Hz, H-7'), 7.22 (1H, t, J=10.0 Hz, H-5); 7.07 (2H, m, H-5', 6), 3.46 (3H, s, N—CH$_3$); CI-MS m/z 295 (M+H)$^+$. Anal. (C$_{17}$H$_{11}$FN$_2$O$_2$) C, H, N.

(2'Z)-7-Chloro-1-methylindirubin (19)

This compound was prepared from 7-chloro-N-methylisatin (IVb) and 3-acetoxyindole by a procedure analogous to that of 7: yield 95%; $^1$H NMR (DMSO, 400 MHz, δ ppm, J in Hz) 10.50 s, N'—H), 8.85 (1H, d, J=7.5 Hz, H-4), 7.67 (1H, d, J=7.4 Hz, H-4'), 7.60 (1H, t, J=7.4 Hz, H-6'), 7.44 (1H, d, J=7.4, Hz, H-7'), 7.32 (1H, d, J=7.4 Hz, H-6), 7.08 (2H, m, H-5, 5'), 3.62 (3H, s, N—CH$_3$); CI-MS m/z 311, 313 (M+H)$^+$. Anal. (C$_{17}$H$_{11}$ClN$_2$O$_2$) C, H, N.

(2'Z)-7-Bromo-1-methylindirubin (27)

This compound was prepared from 7-bromo-N-methylisatin (IVc) and 3-acetoxyindole by a procedure analogous to that of 7: yield 83%; $^1$H NMR (DMSO, 400 MHz, δ ppm, J in Hz) 8.88 (1H, d, J=7.9 Hz, H-4), 7.66 (1H, d, J=7.5 Hz, H-4'), 7.60 (1H, t, J=7.5 Hz, H-6'), 7.47 (1H, d, J=7.5, Hz, H-7'), 7.38 (1H, d, J=7.9 Hz, H-6), 7.04 (2H, m, H-5, 5'), 3.61 (3H, s, N—CH$_3$); CI-MS m/z 355, 357 (M+H)$^+$. Anal. (C$_{17}$H$_{11}$BrN$_2$O$_2$) C, H, N.

(2'Z)-7-Iodo-1-methylindirubin (35)

This compound was prepared from 7-iodo-N-methylisatin (IVd) and 3-acetoxyindole by a procedure analogous to that of 7: yield 87%; $^1$H NMR (DMSO, 400 MHz, δ ppm, J in Hz) 11.26 (1H, s, N'—H), 8.93 (1H, d, J=7.7 Hz, H-4), 7.74 (1H, d, J=7.4 Hz, H-4'), 7.66 (1H, d, J=7.5 Hz, H-6), 7.60 (1H, t, J=7.4, Hz, H-6'), 7.44 (1H, d, J=7.4 Hz, H-7'), 7.05 (1H, t, J=7.4, Hz, H-5'), 6.86 (1H, t, J=7.7, Hz, H-5), 3.65 (3H, s, N—CH$_3$); CI-MS m/z 403 (M+H)$^+$. Anal. (C$_{17}$H$_{11}$N$_2$O$_2$I) C, H, N.

General Procedure for the Preparation of the Oximes 8, 16, 24, 32 and 12, 20, 28, 36, The appropriate indirubin derivative 7, 15, 23, 31 and 11, 19, 27, 35 (1 mmol) was dissolved in pyridine (10 mL). With magnetic stirring, hydroxylamine hydrochloride (10 equiv) was added and the mixture was heated under reflux (120° C.) for 1.5 h. Then the solvent was evaporated under reduced pressure and the residue was washed with water to afford quantitatively the corresponding 3'-oxime selectively in a (2'Z,3'E) form.

Data for (2'Z,3'E)-7-fluoroindirubin-3'-oxime (8)

$^1$H NMR (DMSO, 400 MHz, δ ppm, J in Hz) 13.61 (1H, brs, NOH) 11.85 (1H, s, N'—H), 11.19 (1H, s, N—H), 8.44 (1H, d, J=7.8 Hz, H-4), 8.19 (1H, d, J=7.5, H-4'), 7.39 (2H, m, H-6', 7'), 7.00 (2H, m, H-5', 6), 6.90 (1H, m, H-5); CI-MS m/z 296 (M+H)$^+$. Anal. (C$_{16}$—H$_{10}$N$_3$O$_2$F) C, H, N.

Data for (2'Z,3'E)-7-chloroindirubin-3'-oxime (16)

$^1$H NMR (DMSO, 400 MHz, δ ppm, J in Hz) 13.70 (1H, brs, NOH), 11.86 (1H, s, N'—H), 11.09 (1H, s, N—H), 8.62 (1H, d, J=7.9 Hz, H-4), 8.23 (1H, d, J=7.6, H-4'), 7.44 (2H, m, H-6', 7'), 7.17 (1H, d, J=7.9 Hz, H-6), 7.06 (1H, t, J=7.6 Hz, H-5'), 6.96 (1H, t, J=7.8 Hz, H-5); CI-MS m/Z 312, 314 (M+H)$^+$. Anal. (C$_{16}$H$_{10}$N$_3$O$_2$Cl) C, H, N.

Data for (2'Z,3'E)-7-bromoindirubin-3'-oxime (24)

$^1$H NMR (DMSO, 400 MHz, δ ppm, J in Hz) 13.68 (1H, brs, NOH) 11.90 (1H, s, N'—H), 10.91 (1H, s, N—H), 8.67 (1H, d, J=7.8 Hz, H-4), 8.23 (1H, d, J=7.8, H-4'), 7.42 (2H, m, H-6', 7'), 7.29 (1H, d, J=7.8 Hz, H-6), 7.06 (1H, t, J=7.8 Hz, H-5'), 6.90 (1H, t, J=7.8 Hz, H-5); —CI-MS m/z 356, 358 (M+H)$^+$. Anal. (C$_{16}$H$_{10}$N$_3$O$_2$Br) C, H, N.

Data for (2'Z,3'E)-7-iodoindirubin-3'-oxime (32)

NMR (DMSO, 400 MHz, δ ppm, J in Hz) 13.65 (1H, brs, NOH), 11.87 (1H, s, N'—H), 10.63 (1H, s, N—H), 8.68 (1H, d, J=7.8 Hz, H-4), 8.23 (1H, d, J=7.2, H-4'), 7.47 (1H, J=7.8 Hz, H-6), 7.43 (2H, m, H-6', 7'), 7.06 (1H, t, J=7.2 Hz, H-5'), 6.76 (1H, t, J=7.8 Hz, H-5); CI-MS m/z 404 (M+H)$^+$. Anal. (C$_{16}$H$_{10}$N$_3$O$_2$I) C, H, N.

Data for (2'Z,3'E)-7-fluoro-1-methylindirubin-3'-oxime (12)

$^1$H NMR (DMSO, 400 MHz, δ ppm, J in Hz) 13.72 (1H, brs, NOH), 11.90 (1H, s, N'—H), 8.56 (1H, d, J=7.7 Hz, H-4), 8.23 (1H, d, J=7.6 Hz, H-4'), 7.44 (2H, m, H-6', 7'), 7.07 (1H, m, H-5', 6), 6.97 (1H, m, H-5), 3.60 (3H, s, N—CH$_3$); CI-MS m/z 310 (M+H)$^+$. Anal. (C$_{17}$H$_{12}$N$_3$O$_2$F) C, H, N.

Data for (2'Z,3'E)-7-chloro-1-methylindirubin-3'-oxime (20)

$^1$H NMR (DMSO, 400 MHz, δ ppm, J in Hz) 13.79 (1H, brs, NOH), 11.97 (1H, s, N'—H), 8.76 (1H, d, J=7.8 Hz, H-4), 8.23 (1H, d, J=7.3 Hz, H-4'), 7.45 (2H, m, H-6', 7'), 7.18 (1H, d, J=7.8 Hz, H-6), 7.07 (1H, t, J=7.3 Hz, H-5'), 6.99 (1H, t, J=7.8 Hz, H-5), 3.67 (3H, s, N—CH$_3$); CI-MS m/z 326, 328 (M+H)$^+$. Anal. (C$_{17}$H$_{12}$N$_3$O$_2$Cl) C, H, N.

Data for (2'Z,3'E)-7-bromo-1-methylindirubin-3'-oxime (28)

$^1$H NMR (DMSO, 400 MHz, δ ppm, J in Hz) 12.00 (1H, s, N'—H), 8.81 (1H, d, J=7.9 Hz, H-4), 8.23 (1H, d, J=7.9 Hz, H-4'), 7.43 (2H, m, H-6', 7'), 7.34 (1H, d, J=7.9 Hz, H-6), 7.07 (1H, t, J=7.9 Hz, H-5'), 6.93 (1H, t, J=7.9 Hz, H-5), 3.68 (3H, s, N—CH$_3$); CI-MS m/z 370, 372 (M+H)$^+$. Anal. (C$_{17}$H$_{12}$N$_3$O$_2$Br) C, H, N.

Data for (2'Z,3'E)-7-iodo-1-methylindirubin-3'-oxime (36)

$^1$H NMR (DMSO, 400 MHz, δ ppm, J in Hz) 13.70 (1H, brs, NOH), 12.00 (1H, s, N'—H), 8.85 (1H, d, J=7.7 Hz, H-4), 8.24 (1H, d, J=7.8 Hz, H-4'), 7.60 (1H, d, J=7.7 Hz, H-6), 7.43 (2H, m, H-6', 7'), 7.06 (1H, t, J=7.8 Hz, H-5'), 6.77 (1H, t, J=7.7 Hz, H-5), 3.70 (3H, s, N—CH$_3$); CI-MS m/z 418 (M+H)$^+$. Anal. (C$_{17}$H$_{12}$N$_3$O$_2$I) C, H, N.

General Procedure for the Preparation of the Acetoximes 10, 18, 26, 34 and 14, 22, 30, 38.

The appropriate indirubin-3'-oxime derivatives 8, 16, 24, 32 and 12, 20; 28, 36 (0.2 mmol) were dissolved in pyridine (10 mL). Ac$_2$O was added (0.5 mL) and the mixture was stirred for 30 min at 0° C. Then water (1 mL) was added and the solvents were evaporated under reduced pressure. The residue was washed with water to afford quantitatively the corresponding 3'-acetoxime selectively in a (2'Z,3'E) form.

Data for (2'Z,3'E)-7-fluoroindirubin-3'-acetoxime (10)

$^1$H NMR (DMSO, 400 MHz, δ ppm, J in Hz) 11.68 (1H, s, N'—H), 11.33 (1H, s, N—H), 8.92 (1H, d, J=7.9 Hz, H-4), 8.25 (1H, d, J=7.7, H-4'), 7.51 (2H, m, H-6', 7'), 7.01 (2H, m, H-5', 6), 6.96 (1H, m, H-5), 2.47 (3H, s, OCOCH$_3$); CI-MS m/z 338 (M+H)$^+$. Anal. (C$_{18}$H$_{12}$N$_3$O$_3$F) C, H, N.

Data for (2'Z,3'E)-7-chloroindirubin-3'-acetoxime (18)

$^1$H NMR (DMSO, 400 MHz, δ ppm, J in Hz) 11.70 (1H, s, N'—H), 11.23 (1H, s, N—H), 9.07 (1H, d, J=8.0 Hz, H-4), 8.25 (1H, d, J=7.6, H-4'), 7.52 (2H, m, H-6', 7'), 7.24 (1H, d, J=8.0 Hz, H-6), 7.11 (1H, t, J=7.6 Hz, H-5'), 6.97 (1H, t, J=8.0 Hz, H-5), 2.47 (3H, s, OCOCH$_3$); CI-MS m/z 354, 356 (M+H)$^+$. Anal. (C$_{18}$H$_{12}$N$_3$O$_3$Cl) C, H, N.

Data for (2'Z,3'E)-7-bromoindirubin-3'-acetoxime (26)

$^1$H NMR (DMSO, 400 MHz, δ ppm, J in Hz) 11.73 (1H, s, N'—H), 11.11 (1H, s, N—H), 9.12 (1H, d, J=7.5 Hz, H-4), 8.27 (1H, d, J=7.9, H-1-4'), 7.53 (2H, m, H-6', 7'), 7.37 (1H, d, J=7.5 Hz, H-6), 7.11 (1H, t, J=7.9 Hz, H-5'), 6.92 (1H, t, J=7.5 Hz, H-5), 2.48 (3H, s, OCOCH$_3$); CI-MS m/z 398, 400 (M+H)$^+$. Anal. (C$_{18}$H$_{12}$N$_3$O$_3$Br) C, H, N.

Data for (2'Z,3'E)-7-iodoindirubin-3'-acetoxime (34)

$^1$H NMR (DMSO, 400 MHz, δ ppm, J in Hz) 11.71 (1H, s, N'—H), 10.78 (1H, s, N—H), 9.12 (1H, d, J=7.9 Hz, H-4), 8.25 (1H, d, J=7.5, H-4'), 7.52 (3H, m, H-6, 6', 7'), 7.10 (1H, t, J=7.5 Hz, H-5'), 6.77 (1H, t, J=7.9 Hz, H-5), 2.47 (3H, s, OCOCH$_3$); CI-MS m/z 446 (M+H)$^+$. Anal. (C$_{18}$H$_{12}$N$_3$O$_3$I) C, H, N.

Data for (2'Z,3'E)-7-fluoro-1-methylindirubin-3'-acetoxime (14)

$^1$H NMR (DMSO, 400 MHz, δ ppm, J in Hz) 11.76 (1H, s, N'—H), 9.00 (1H, d, J=8.0 Hz, H-4), 8.26 (1H, d, J=7.4 Hz, H-4'), 7.53 (2H, m, H-6', 7'), 7.12 (2H, m, H-5', 6), 7.00 (1H, m, H-5), 3.50 (3H, s, N—CH$_3$), 2.47 (3H, s, OCOCH$_3$); CI-MS m/z 352 (M+H)$^+$. Anal. (C$_{19}$H$_{14}$N$_3$O$_3$F) C, H, N.

Data for (2'Z,3'E)-7-chloro-1-methylindirubin-3'-acetoxime (22)

$^1$H NMR (DMSO, 400 MHz, δ ppm, J in Hz) 11.83 (1H, s, N'—H), 9.20 (1H, d, J=8.0 Hz, H-4), 8.27 (1H, d, J=7.5 Hz, H-4'), 7.52 (2H, m, H-6', 7'), 7.26 (1H, d, J=8.0 Hz, H-6), 7.12 (1H, t, J=7.5 Hz, H-5'), 7.01 (1H, t, J=8.0 Hz, H-5), 3.66 (3H, s, N—CH$_3$), 2.47 (3H, s, OCOCH$_3$); CI-MS m/z 368, 370 (M+H)$^+$. Anal. (C$_{19}$H$_{14}$N$_3$O$_3$Cl) C, H, N.

Data for (2'Z,3'E)-7-bromo-1-methylindirubin-3'-acetoxime (30)

$^1$H NMR (DMSO, 400 MHz, δ ppm, J in Hz) 11.83 (1H, s, N'—H), 9.24 (1H, d, J=7.9 Hz, H-4), 8.26 (1H, d, J=7.5 Hz, H-4'), 7.54 (1H, d, J=7.5 Hz, H-7'), 7.51 (1H, t, J=7.5 Hz, H-6'), 7.41 (1H, d, J=7.9 Hz, H-6), 7.12 (1H, t, J=7.5 Hz, H-5'), 6.94 (1H, t, J=7.9 Hz, H-5), 3.67 (3H, s, N—CH$_3$), 2.47 (3H, s, OCOCH$_3$); CI-MS m/z 412, 414 (M+H)$^+$. Anal. (C$_{19}$H$_{14}$N$_3$O$_3$Br) C, H, N.

Data for (2'Z,3'E)-7-iodo-1-methylindirubin-3'-acetoxime (38)

$^1$H NMR (DMSO, 400 MHz, δ ppm, J in Hz) 11.81 (1H, s, N'—H), 9.26 (1H, d, J=7.8 Hz, H-4), 8.25 (1H, d, J=7.5 Hz, H-4'), 7.68 (1H, d, J=7.8 Hz, H-6), 7.52 (2H, m, H-6', 7'), 7.11 (1H, t, J=7.5 Hz, H-5'), 6.78 (1H, t, J=7.8 Hz, H-5), 3.68 (3H, s, N—CH$_3$), 2.47 (3H, s, OCOCH$_3$); CI-MS m/z 460 (M+H)$^+$. Anal. (C$_{19}$H$_{14}$N$_3$O$_3$I) C, H, N.

General Procedure for the Preparation of the Methoximes 9, 17, 25, 33 and 13, 21, 29, 37.

The appropriate indirubin derivatives 7, 15, 23, 31 and 11, 19, 27, 35 (1 mmol) were dissolved in pyridine (10 mL). With magnetic stirring, methoylamine hydrochloride (10 equiv) was added and the mixture was heated under reflux (120° C.) for 1.5 h. Then the solvent was evaporated under reduced pressure and the residue was washed with water to afford quantitatively the corresponding 3'-methoxime selectively in a (2'Z,3'E) form.

Data for (2'Z,3'E)-7-Fluoroindirubin-3'-methoxime (9)

$^1$H NMR (DMSO, 400 MHz, δ ppm, J in Hz) 11.79 (1H, s, N'—H), 11.24 (1H, s, N—H), 8.46 (1H, d, J=7.5 Hz, H-4), 8.12 (1H, d, J=7.6, H-4'), 7.44 (2H, m, H-6', 7'), 7.05 (3H, m, H-5, 5', 6), 4.39 (3H, s, OCH$_3$); CI-MS m/z 310 (M+H)$^+$. Anal. (C$_{17}$H$_{12}$N$_3$O$_2$F) C, H, N.

Data for (2'Z,3'E)-7-Chloroindirubin-3'-methoxime (17)

$^1$H NMR (DMSO, 400 MHz, δ ppm, J in Hz) 11.82 (1H, s, N'—H), 11.24 (1H, s, N—H), 8.60 (1H, d, J=7.9 Hz, H-4), 8.12 (1H, d, J=7.9, H-4'), 7.46 (2H, m, H-6', 7'), 7.20 (1H, d, J=7.9 Hz, H-6), 7.05 (2H, m, H-5, 5'), 4.40 (3H, s, OCH$_3$); CI-MS m/z 326, 328 (M+H)$^+$. Anal. (C$_{17}$H$_{12}$N$_3$O$_2$Cl) C, H, N.

Data for (2'Z,3'E)-7-Bromoindirubin-3'-methoxime (25)

$^1$H NMR (DMSO, 400 MHz, δ ppm, J in Hz) 11.84 (1H, s, N'—H), 11.02 (1H, s, N—H), 8.65 (1H, d, J=7.9 Hz, H-4), 8.13 (1H, d, J=7.9, H-4'), 7.46 (2H, m, H-6', 7'), 7.34 (1H, d, J=7.9 Hz, H-6), 7.06 (1H, m, H-5'), 6.97 (1H, t, J=7.9, H-5), 4.41 (3H, s, OCH$_3$); CI-MS m/z 370, 372 (M+H)$^+$. Anal. (C$_{17}$H$_{22}$N$_3$O$_2$Br) C, H, N.

Data for (2'Z,3'E)-7-Iodoindirubin-3'-methoxime (33)

$^1$H NMR (DMSO, 400 MHz, δ ppm, J in Hz) 11.82 (1H, s, N'—H), 10.69 (1H, s, N—H), 8.66 (1H, d, J=7.8 Hz, H-4), 8.12 (1H, d, J=7.7, H-4'), 7.50 (1H, d, J=7.8 Hz, H-6), 7.45 (2H, m, H-6', 7'), 7.06 (1H, m, H-5'), 6.82 (1H, t, J=7.8, H-5), 4.39 (3H, s, OCH$_3$); CI-MS m/z 418 (M+H)$^+$. Anal. (C$_{17}$H$_{12}$N$_3$O$_2$I) C, H, N.

Data for (2'Z,3'E)-7-fluoro-1-methylindirubin-3'-methoxime (13)

$^1$H NMR (DMSO, 400 MHz, δ ppm, J in Hz) 11.83 (1H, s, N'—H), 8.52 (1H, d, J=7.4 Hz, H-4), 8.10 (1H, d, J=7.6 Hz, H-4'), 7.44 (2H, m, H-6', 7'), 7.06 (3H, m, H-5, 5', 6), 4.39 (3H, s, OCH$_3$), 3.48 (3H, s, N—CH$_3$); CI-MS m/z 324 (M+H)$^+$. Anal. (C$_{18}$H$_{14}$N$_3$O$_2$F) C, H, N.

Data for (2'Z,3'E)-7-chloro-1-methylindirubin-3'-methoxime (21)

$^1$H NMR (DMSO, 400 MHz, δ ppm, J in Hz) 11.91 (1H, s, N'—H), 8.72 (1H, d, J=7.8 Hz, H-4), 8.11 (1H, d, J=7.8 Hz, H-4'), 7.46 (2H, m, H-6', 7'), 7.21 (1H, d, J=7.8 Hz, H-6), 7.05 (2H, m, H-5, 5'), 4.40 (3H, s, OCH$_3$), 3.66 (3H, s, N—CH$_3$); CI-MS m/z 340, 342 (M+H)$^+$. Anal. (C$_{18}$H$_{14}$N$_3$O$_2$Cl) C, H, N.

Data for (2'Z,3'E)-7-bromo-1-methylindirubin-3'-methoxime (29)

$^1$H NMR (DMSO, 400 MHz, δ ppm, J in Hz) 11.94 (1H, s, N'—H), 8.80 (1H, d, J=7.9 Hz, H-4), 8.13 (1H, d, J=7.1 Hz, H-4'), 7.47 (2H, m, H-6', 7'), 7.38 (1H, d, J=7.9 Hz, H-6), 7.07 (1H, m, H-5'), 7.00 (1H, t, J=7.9 Hz, H-5), 4.40 (3H, s, OCH$_3$), 3.68 (3H, s, N—CH$_3$); CI-MS m/z 384, 386 (M+H)$^+$. Anal. (C$_{18}$H$_{14}$N$_3$O$_2$Br) C, H, N.

Data for (2'Z,3'E)-7-iodo-1-methylindirubin-3'-methoxime (37)

$^1$H NMR (DMSO, 400 MHz, δ ppm, J in Hz) 11.92 (1H, s, N'—H), 8.81 (1H, d, J=7.7 Hz, H-4), 8.12 (1H, d, J=7.7 Hz, H-4'), 7.64 (1H, d, J=7.7 Hz, H-6), 7.50 (2H, m, H-6', 7'), 7.06 (1H, m, H-5'), 6.83 (1H, t, J=7.7 Hz, H-5), 4.39 (3H, s, OCH$_3$), 3.68 (3H, s, N—CH$_3$); CI-MS m/z 432 (M+H)$^+$. Anal. (C$_{18}$H$_{14}$N$_3$O$_2$I) C, H, N.

(2'Z,3'E)-7-bromoindirubin-3'[O-(2-bromoethyl)-oxime] (57)

To a solution of 7BIO (24) (100 mg, 0.30 mmol) in 5 mL of anhydrous DMF, 120 μL of triethylamine (2.9 equiv) and 72 μl, of 1,2 dibromoethane (2.8 equiv) were added and the reaction mixture was stirred under Ar at room temperature for 48 h. Then, the solvent was evaporated under reduced pressure and the residue was washed with water and dried at 50° C. to afford in 95% yield the corresponding 3'-substituted oxime 57. $^1$H NMR (DMSO, 400 MHz, δ ppm, J in Hz) 11.81 (1H, s, N'—H), 11.02 (1H, s, N—H), 8.59 (1H, d, J=8.0 Hz, H-4), 8.22 (1H, d, J=8.0 Hz, H-4'), 7.47 (2H, m, Hz, H-6', 7'), 7.33 (1H, d, J=8.0 Hz, H-6), 7.08 (1H, m, H-5'), 6.95 (1H, t, J=8.0 Hz, H-5), 4.93 (2H, t, J=5.4 Hz, H-1''), 3.98 (2H, t, J=5.4 Hz, H-2''); CI-MS m/z 463, 465, 467 (M+H)$^+$. Anal. (C$_{18}$H$_{13}$N$_3$O$_2$Br$_2$) C, H, N.

(2'Z,3'E)-1-methyl-7-bromoindirubin-3'-[O-(2-bromoethyl)-oxime] (58)

This compound was prepared from Me7BIO (27) by a procedure analogous to that of 57; $^1$H NMR (DMSO, 400 MHz, δ ppm, J in Hz) 11.92 (1H, s, N'—H), 8.74 (1H, d, J=8.1 Hz, H-4), 8.22 (1H, d, J=8.0 Hz, H-4'), 7.47 (2H, m, H-6', 7'), 7.38 (1H, d, J=8.1 Hz, H-6), 7.09 (1H, m, H-5'), 6.98 (1H, t, J=8.1 Hz, H-5), 4.94 (2H, t, J=5.3 Hz, H-1''), 3.98 (2H, t, J=5.3 Hz, H-2''), 3.68 (3H, s, N—CH$_3$); CI-MS m/z 477, 479, 481 (M+H)$^+$. Anal. (C$_{19}$H$_{15}$N$_3$O$_2$Br$_2$) C, H, N.

(2'Z,3'E)-7-bromoindirubin-3'-[O—(N,N-diethylcarbamyl)-oxime](63)

To a solution of 7BIO (24) (25 mg, 0.07 mmol) in anhydrous DMF (3 mL), 14 μL of triethylamine (1.5 equiv) and 13 μL of N,N-diethylcarbamyl chloride (1.5 equiv) were added and the reaction mixture was stirred under Ar at room temperature for 48 h. Then, the solvent was evaporated under reduced pressure and the residue was washed with water and dried at 50° C. to afford quantitatively the corresponding 3'-substituted oximes. $^1$H NMR (C$_5$D$_5$N, 400 MHz, δ ppm, J in Hz) 12.70 (1H, s, N'—H), 12.29 (1H, s, N—H), 10.04 (1H, d, J=7.6 Hz, H-4), 8.18 (1H, d, J=7.6 Hz, H-6), 7.49 (2H, m, H-4', 6'), 7.34 (1H, t, J=7.9 Hz, H-5'), 7.22 (1H, overlapped, H-7'), 7.14 (1H, t, J=7.6 Hz, H-5), 3.46 (4H, brs, N(CH$_2$CH$_3$)$_2$), 1.19 (6H, t, J=6.5 Hz, N(CH$_2$CH$_3$)$_2$); CI-MS m/z 455, 457 (M+H)$^+$. Anal. (C$_{21}$H$_{19}$N$_4$O$_3$Br) C, H, N.

Data for (2'Z,3'E)-1-methyl-7-bromoindirubin-3'-[O—(N,N-diethylcarbamyl)-oxime](64)

This compound was prepared from Me7BIO (27) by a procedure analogous to that of 63. $^1$H NMR (C$_5$D$_5$N, 400 MHz, δ ppm, J in Hz) 12.32 (1H, s, N'—H), 10.10 (1H, d, J=7.6 Hz, H-4), 8.18 (1H, d, J=7.6 Hz, H-6), 7.46 (2H, m, H-4', 6'), 7.30 (1H, t, J=7.8 Hz, H-5'), 7.16 (2H, overlapped, H-5, 7'), 3.66 (3H, s, N—CH$_3$), 3.46 (4H, brs, N(CH$_2$CH$_3$)$_2$), 1.19 (6H, t, J=6.8 Hz, N(CH$_2$CH$_3$)$_2$); CI-MS m/z 469, 471 (M+H)$^+$. Anal. (C$_{22}$H$_{21}$N$_4$O$_3$Br) C, H, N.

General Procedure for the Preparation of 3'-Substituted Oximes of 7BIO or Me7BIO (39-62)

7-Bromoindirubin-3'-[O-(2-bromoethyl)-oxime] (57) or 1-methyl-7-bromoindirubin-3'[O-(2-bromoethyl)-oxime] (58) (25 mg, 0.05 mmol) were dissolved in 3 mL of anhydrous DMF. The corresponding amine (pyrrolidine, morpholine, imidazole, piperazine, dimethylamine and diethylamine), (30 equiv) was added and the reaction mixture was stirred under Ar at room temperature for 48 h. Then the solvent was evaporated under reduced pressure and the residue was washed with water and dried at 50° C. to afford the corresponding 3'-substituted oximes with 75-90% yield. For the preparation of the hydrochloric salts of the above compounds, 10 mg of each compound was dissolved in 5 mL of anhydrous tetrahydrofuran. Then, a solution of hydrochloric acid in diethylether was added slowly and the formed precipitate was filtered, washed with dichloromethane and dried at 50° C. to afford the corresponding hydrochloric salts.

Data for (2'Z,3'E)-7-bromoindirubin-3'-[O-(2-pyrrolidin-1-yl-ethyl)-oxime](39)

Yield: 90%; $^1$H NMR (DMSO, 400 MHz, δ ppm, J in Hz) 11.82 (1H, s, N'—H), 11.00 (1H, s, N—H), 8.64 (1H, d, J=8.0 Hz, H-4), 8.15 (1H, d, J=7.7 Hz, H-4'), 7.45 (2H, m, H-6', 7'), 7.33 (1H, d, J=8.0 Hz, H-6), 7.07 (1H, ddd, J=7.7, 5.5, 3.1 Hz, H-5'), 6.94 (1H, t, J=8.0 Hz, H-5), 4.70 (2H, t, J=5.9 Hz, H-1''), 2.98 (2H, t, J=5.9 Hz, H-2''), 2.56 (4H, m, H-2''', 5'''), 1.68 (4H, m, H-3''', 4'''); CI-MS m/z 453, 455 (M+H)$^+$. Anal. (C$_{22}$H$_{21}$N$_4$O$_2$Br) C, H, N.

Data for (2'Z,3'E)-7-bromoindirubin-3'-[O-(2-pyrrolidin-1-yl-ethyl)-oxime]hydrochloride (40)

$^1$H NMR (DMSO, 400 MHz, δ ppm, J in Hz) 11.84 (1H, s, N'—H), 11.06 (1H, s, N—H), 10.31 (1H, brs, N'''—H), 8.58 (1H, d, J=7.9 Hz, H-4), 8.24 (1H, d, J=8.3 Hz, H-4'), 7.49 (2H, m, H-6', 7'), 7.37 (1H, d, J=7.9 Hz, H-6), 7.09 (1H, ddd, J=8.3, 4.4, 1.3 Hz, H-5'), 6.99 (1H, t, J=7.9 Hz, H-5), 4.97 (2H, brs, H-1''), 3.77 (2H, brs, H-2''), 3.64 (2H, m, H-2'''a, 5'''a), 3.12

(2H, m, 2'''b, 5'''b), 2.00 (2H, m, H-3'''a, 4'''a), 1.86 (2H, m, H-3'''b, 4'''b); Anal. (C$_{22}$H$_{22}$N$_4$O$_2$BrCl) C, H, N.

Data for (2'Z,3'E)-1-methyl-7-bromoindirubin-3'-[O-(2-pyrrolidin-1-yl-ethyl)-oxime](41)

Yield: 90%; $^1$H NMR (DMSO, 400 MHz, δ ppm, J in Hz) 11.93 (1H, s, N'—H), 8.80 (1H, d, J=7.9 Hz, H-4), 8.16 (1H, d, J=8.0 Hz, H-4'), 7.46 (2H, m, H-6', 7'), 7.37 (1H, d, J=7.9 Hz, H-6), 7.07 (1H, ddd, J=8.0, 5.5, 3.1 Hz, H-5'), 6.97 (1H, t, J=7.9 Hz, H-5), 4.71 (2H, t, J=5.9 Hz, H-1''), 3.68 (3H, s, N—CH$_3$), 2.98 (2H, t, J=5.9 Hz, H-2''), 2.56 (4H, m, H-2''', 5'''), 1.68 (4H, m, H-3''', 4'''); CI-MS m/z 467, 469 (M+H)$^+$. Anal. (C$_{23}$H$_{23}$N$_4$O$_2$Br) C, H, N.

Data for (2'Z,3'E)-1-methyl-7-bromoindirubin-3'-[O-(2-pyrrolidin-1-yl-ethyl)-oxime]hydrochloride (42)

$^1$H NMR (DMSO, 400 MHz, δ ppm, J in Hz) 11.94 (1H, s, N'—H), 10.05 (1H, brs, N'''—H), 8.73 (1H, d, J=7.8 Hz, H-4), 8.24 (1H, d, J=7.8 Hz, H-4'), 7.49 (2H, m, H-6', 7'), 7.40 (1H, d, J=7.8 Hz, H-6), 7.09 (1H, ddd, J=7.8, 4.1, 1.7 Hz, H-5'), 7.01 (1H, t, J=7.8 Hz, H-5), 4.96 (2H, m, H-1''), 3.68 (3H, s, N—CH$_3$), 3.64 (2H, m, H-2'''a, 5'''a), 3.14 (2H, m, 2'''b, 5'''b), 2.00 (2H, m, H-3'''a, 4'''a), 1.85 (2H, m, H-3'''b, 4'''b); Anal. (C$_{23}$H$_{24}$N$_4$O$_2$BrCl) C, H, N.

Data for (2'Z,3'E)-7-bromoindirubin-3'-[O-(2-morpholin-1-yl-ethyl)-oxime](43)

Yield: 85%; $^1$H NMR (C$_5$D$_5$N, 400 MHz, δ ppm, J in Hz) 12.68 (1H, s, N'—H), 12.40 (1H, s, N—H), 9.02 (1H, d, J=7.7 Hz, H-4), 8.42 (1H, d, J=7.7 Hz, H-6), 7.54 (1H, d, J=7.7 Hz, H-4'), 7.42 (1H, t, J=7.7 Hz, H-6'), 7.18 (2H, overlapped, H-5', H-7'), 7.10 (1H, t, J=7.7 Hz, H-5), 4.80 (2H, t, J=5.9 Hz, H-1''), 3.76 (4H, t, J=4.2 Hz, H-3''', 5'''), 2.94 (2H, t, J=5.9 Hz, H-2''), 2.60 (4H, t, J=4.2 Hz, H-2''', 6'''); CI-MS m/z 469, 471 (M+H)$^+$. Anal. (C$_{22}$H$_{21}$N$_4$O$_3$Br) C, H, N.

Data for (2'Z,3'E)-7-bromoindirubin-3'-[O-(2-morpholin-1-yl-ethyl)-oxime]hydrochloride (44)

$^1$H NMR (DMSO, 400 MHz, δ ppm, J in Hz) 11.82 (1H, s, N'—H), 11.04 (1H, s, N—H), 10.71 (1H, brs, N''''—H), 8.58 (1H, d, J=7.9 Hz, H-4), 8.23 (1H, d, J=7.7 Hz, H-4'), 7.47 (2H, m, H-6', 7'), 7.35 (1H, d, J=7.9 Hz, H-6), 7.08 (1H, ddd, J=7.7, 5.8, 2.3 Hz, H-5'), 6.99 (1H, t, J=7.9 Hz, H-5), 5.02 (2H, m, H-1''), 3.95 (2H, m, H-3'''a, 5'''a), 3.74 (4H, overlapped, H-2'', 3'''b, 5'''b), 3.57 (2H, m, H-2'''a, 6'''a), 3.25 (2H, overlapped, 2'''b, 6'''b); Anal. (C$_{22}$H$_{22}$N$_4$O$_3$BrCl) C, H, N.

Data for (2'Z,3'E)-1-methyl-7-bromoindirubin-3'-[O-(2-morpholin-1-yl-ethyl)-oxime] (45)

Yield: 85%; $^1$H NMR (C$_5$D$_5$N, 400 MHz, δ ppm, J in Hz) 12.40 (1H, s, N'—H), 9.11 (1H, d, J=7.8 Hz, H-4), 8.42 (1H, d, J=7.7 Hz, H-6), 7.49 (1H, d, J=7.7 Hz, H-4'), 7.40 (1H, m, H-6', 7'), 7.10 (1H, m, H-5, 5'), 4.81 (2H, t, J=5.9 Hz, H-1''), 3.76 (4H, t, J=4.5 Hz, H-3''', 5'''), 3.70 (3H, s, N—CH$_3$), 2.94 (2H, t, J=5.9 Hz, H-2''), 2.60 (4H, t, J=4.5 Hz, H-2''', 6'''); CI-MS m/z 483, 485 (M+H)$^+$. Anal. (C$_{23}$H$_{23}$N$_4$O$_3$Br) C, H, N.

Data for (2'Z,3'E)-1-methyl-7-bromoindirubin-3'-[O-(2-morpholin-1-yl-ethyl)-oxime]hydrochloride (46)

$^1$H NMR (DMSO, 400 MHz, δ ppm, J in Hz) 11.94 (1H, s, N'—H), 10.52 (1H, brs, N''''—H), 8.73 (1H, d, J=8.0 Hz, H-4), 8.23 (1H, d, J=7.7 Hz, H-4'), 7.49 (2H, m, H-6', 7'), 7.40 (1H, d, J=8.0 Hz, H-6), 7.09 (1H, ddd, J=7.7, 4.1, 1.0 Hz, H-5'), 7.01 (1H, t, J=8.0 Hz, H-5), 5.02 (2H, m, H-1''), 3.98 (2H, m, H-3'''a, 5'''a), 3.72 (4H, overlapped, H-2'', 3'''b, 5'''b), 3.68 (3H, s, N—CH$_3$), 3.55 (2H, m, H-2'''a, 6'''a), 3.26 (2H, overlapped, 2'''b, 6'''b); Anal. (C$_{23}$H$_{24}$N$_4$O$_3$BrCl) C, H, N.

Data for (2'Z,3'E)-7-bromoindirubin-3'-[O-(2-imidazol-1-yl-ethyl)-oxime](47)

Yield: 75%; $^1$H NMR (DMSO, 400 MHz, δ ppm, J in Hz) 11.79 (1H, s, N'—H), 10.99 (1H, s, N—H), 8.51 (1H, d, J=8.0 Hz, H-4), 7.99 (1H, d, J=7.4 Hz, H-4'), 7.67 (1H, s, H-2'''), 7.44 (2H, m, H-6', 7'), 7.33 (1H, d, J=8.0 Hz, H-6), 7.27 (1H, s, H-4'''), 7.02 (1H, ddd, J=8.0, 5.5, 3.1 Hz, H-5'), 6.96 (1H, t, J=8.0 Hz, H-5), 6.87 (1H, s, H-5'''), 4.90 (2H, t, J=4.2 Hz, H-1''), 4.54 (2H, t, J=4.2 Hz, H-2''); CI-MS m/z 450, 452 (M+H)$^+$. Anal. (C$_{21}$H$_{16}$N$_5$O$_2$Br) C, H, N.

Data for (2'Z,3'E)-7-bromoindirubin-3'-[O-(2-imidazol-1-yl-ethyl)-oxime]hydrochloride (48)

$^1$H NMR (DMSO, 400 MHz, δ ppm, J in Hz) 11.79 (1H, s, N'—H), 11.02 (1H, s, N—H), 9.19 (1H, s, H-2'''), 8.40 (1H, d, J=7.9 Hz, H-4), 7.95 (1H, d, J=7.5 Hz, H-4'), 7.86 (1H, s, H-5'''), 7.62 (1H, s, H-4'''), 7.44 (2H, m, H-6', 7'), 7.35 (1H, d, J=7.9 Hz, H-6), 6.94-7.04 (2H, overlapped, 5'), 5.04 (2H, t, J=4.6 Hz, H-1''), 4.77 (2H, t, J=4.6 Hz, H-2''); Anal. (C$_{21}$H$_{17}$N$_5$O$_2$BrCl) C, H, N.

Data for (2'Z,3'E)-1-methyl-7-bromoindirubin-3'-[O-(2-imidazol-1-yl-ethyl)-oxime](49)

Yield: 76%; $^1$H NMR (DMSO, 400 MHz, δ ppm, J in Hz) 11.89 (1H, s, N'—H), 8.65 (1H, d, J=8.0 Hz, H-4), 7.99 (1H, d, J=8.1 Hz, H-4'), 7.69 (1H, s, H-2'''), 7.45 (2H, m, H-6', 7'), 7.37 (1H, d, J=8.0 Hz, H-6), 7.26 (1H, s, H-4'''), 6.97-7.05 (2H, overlapped, H-5', 5), 6.86 (1H, s, H-5'''), 4.90 (2H, t, J=4.8 Hz, H-1''), 4.54 (2H, t, J=4.8 Hz, H-2''), 3.67 (3H, s, N—CH$_3$); CI-MS m/z 464, 466 (M+H)$^+$. Anal. (C$_{22}$H$_{18}$N$_5$O$_2$Br) C, H, N.

Data for (2'Z,3'E)-1-methyl-7-bromoindirubin-3'-[O-(2-imidazol-1-yl-ethyl)-oxime]hydrochloride (50)

$^1$H NMR (DMSO, 400 MHz, δ ppm, J in Hz) 11.90 (1H, s, N'—H), 9.11 (1H, s, H-2'''), 8.55 (1H, d, J=7.9 Hz, H-4), 7.96 (1H, d, J=7.6 Hz, H-4'), 7.83 (1H, s, H-5'''), 7.58 (1H, s, H-4'''), 7.46 (2H, m, H-6', 7'), 7.40 (1H, d, J=7.9 Hz, H-6), 6.97-7.05 (2H, overlapped, H-5, 5'), 5.04 (2H, t, J=4.6 Hz, H-1''), 4.75 (2H, t, J=4.6 Hz, H-2''), 3.67 (3H, s, N—CH$_3$); Anal. (C$_{22}$H$_{19}$N$_5$O$_2$BrCl) C, H, N.

Data for (2'Z,3'E)-7-bromoindirubin-3'-[O-(2-piperazin-1-yl-ethyl)-oxime](51)

Yield: 84%; $^1$H NMR (DMSO, 400 MHz, δ ppm, J in Hz) 11.82 (1H, s, N'—H), 11.00 (1H, s, N—H), 8.63 (1H, d, J=8.0 Hz, H-4), 8.17 (1H, d, J=7.8 Hz, H-4'), 7.45 (2H, m, H-6', 7'), 7.33 (1H, d, J=8.0 Hz, H-6), 7.06 (1H, ddd, J=7.8, 5.1, 3.1 Hz, H-5'), 6.94 (1H, t, J=8.0 Hz, H-5), 4.71 (2H, t, J=5.6 Hz, H-1''), 2.87 (2H, t, J=5.6 Hz, H-2''), 2.68 (4H, t, J=4.6 Hz, H-2''', 6'''), 2.44 (4H, brs, H-3''', 5'''); CI-MS m/z 468, 470 (M+H)$^+$. Anal. (C$_{22}$H$_{22}$N$_5$O$_2$Br) C, H, N.

Data for (2'Z,3'E)-7-bromoindirubin-3'-[O-(2-piperazin-1-yl-ethyl)-oxime]dihydrochloride (52)

$^1$H NMR-(DMSO, 400 MHz, δ ppm, J in Hz) 11.82 (1H, s, N'—H), 11.05 (1H, s, N—H), 9.32 (2H, br, piperazine N$^+$—H), 8.59 (1H, d, J=8.0 Hz, H-4), 8.25 (1H, d, J=7.5 Hz, H-4'), 7.48 (2H, m, H-6', 7'), 7.35 (1H, d, J=8.0 Hz, H-6), 7.06

(1H, ddd, J=7.5, 4.1, 1.4 Hz, H-5'), 6.99 (1H, t, J=8.0 Hz, H-5), 4.98 (2H, m, H-1''), 3.70 (2H, m, H-2''), 8H, overlapped, H-2''', 3''', 5''', 6'''; Anal. ($C_{22}H_{24}N_5O_2BrCl_2$) C, H, N.

Data for (2'Z,3'E)-7-bromoindirubin-3'-[O-(2-dimethylaminoethyl)-oxime](53)

Yield: 90%; $^1$H NMR (DMSO, 400 MHz, δ ppm, J in Hz) 11.82 (1H, s, N'—H), 11.00 (1H, s, N—H), 8.65 (1H, d, J=8.0 Hz, H-4), 8.15 (1H, d, J=7.8 Hz, H-4'), 7.46 (2H, m, H-6', 7'), 7.33 (1H, d, J=8.0 Hz, H-6), 7.07 (1H, ddd, J=7.8, 5.1, 3.4 Hz, H-5'), 6.94 (1H, t, J=8.0 Hz, H-5), 4.70 (2H, t, J=5.9 Hz, H-1''), 2.81 (2H, t, J=5.9 Hz, H-2''), 2.26 (6H, s, N''' ($CH_3$)$_2$); CI-MS m/z 433, 435 (M+H)$^+$. Anal. ($C_{20}H_{25}N_4O_2Br$) C, H, N.

Data for (2'Z,3'E)-7-bromoindirubin-3'-[O-(2-dimethylaminoethyl)-oxime]hydrochloride (54)

$^1$H NMR (DMSO, 400 MHz, δ ppm, J in Hz) 11.83 (1H, s, N'—H), 11.04 (1H, s, N—H), 9.74 (1H, brs, N'''—H), 8.58 (1H, d, J=8.0 Hz, H-4), 8.23 (1H, d, J=7.7 Hz, H-4'), 7.48 (2H, m, H-6', 7'), 7.36 (1H, d, J=8.0 Hz, H-6), 7.07 (1H, ddd, J=7.7, 5.0, 3.3 Hz, H-5'), 6.97 (1H, t, J=8.0 Hz, H-5), 4.94 (2H, t, J=5.9 Hz, H-1''), 3.64 (2H, t, J=5.9 Hz, H-2''), 2.85 (6H, s, N'''($CH_3$)$_2$); Anal. ($C_{20}H_{26}N_4O_2BrCl$) C, H, N.

Data for (2'Z,3'E)-1-methyl-7-bromoindirubin-3'-[O-(2-dimethylaminoethyl)-oxime](55)

Yield: 90%; $^1$H NMR (DMSO, 400 MHz, δ ppm, J in Hz) 11.94 (1H, s, N'—H), 8.80 (1H, d, J=7.9 Hz, H-4), 8.16 (1H, d, J=7.8 Hz, H-4'), 7.47 (2H, m, H-6', 7'), 7.38 (1H, d, J=7.9 Hz, H-6), 7.08 (1H, ddd, J=7.8, 5.5, 2.6 Hz, H-5'), 6.97 (1H, t, J=7.9 Hz, H-5), 4.70 (2H, t, J=5.8 Hz, H-1''), 3.68 (3H, s, N—$CH_3$), 2.81 (2H, t, J=5.8 Hz, H-2''), 2.26 (6H, s, N''' ($CH_3$)$_2$); CI-MS m/z 447, 449 (M+H)$^+$. Anal. ($C_{21}H_{27}N_4O_2Br$) C, H, N.

Data for (2'Z,3'E)-1-methyl-7-bromoindirubin-3'-[O-(2-dimethylaminoethyl)-oxime]hydrochloride (56)

$^1$H NMR (DMSO, 400 MHz, δ ppm, J in Hz) 11.94 (1H, s, N'—H), 10.07 (1H, brs, N'''—H), 8.73 (1H, d, J=8.1 Hz, H-4), 8.25 (1H, d, J=7.7 Hz, H-4'), 7.49 (2H, m, H-6', 7'), 7.40 (1H, d, J=8.1 Hz, H-6), 7.09 (1H, ddd, J=7.7, 5.5, 3.5 Hz, H-5'), 7.02 (1H, t, J=8.1 Hz, H-5), 5.00 (2H, t, J=5.8 Hz, H-1'') 3.68 (3H, s, N—$CH_3$), 3.64 (2H, t, J=5.8 Hz, H-2''), 2.85 (6H, s, N'''($CH_3$)$_2$); Anal. ($C_{21}H_{28}N_4O_2BrCl$) C, H, N.

Data for (2'Z,3'E)-7-bromoindirubin-3'-[O-(2-diethylaminoethyl)-oxime](59)

Yield: 89%; $^1$H NMR (DMSO, 400 MHz, δ ppm, J in Hz) 11.83 (1H, s, N'—H), 11.00 (1H, s, N—H), 8.66 (1H, d, J=7.9 Hz, H-4), 8.17 (1H, d, J=7.8 Hz, H-4'), 7.45 (2H, m, H-6', 7'), 7.33 (1H, d, J=7.9 Hz, H-6), 7.06 (1H, ddd, J=7.8, 5.5, 3.4 Hz, H-5'), 6.93 (1H, t, J=7.9 Hz, H-5), 4.66 (2H, t, J=6.1 Hz, H-1''), 2.95 (2H, t, J=6.1 Hz, H-2''), 2.59 (4H, q, J=7.1 Hz, N'''($CH_2CH_3$)$_2$), 0.98 (6H, t, J=7.1 Hz, N''' ($CH_2CH_3$)$_2$); CI-MS m/z 461, 463 (M+H)$^+$. Anal. ($C_{22}H_{29}N_4O_2Br$) C, H, N.

Data for (2'Z,3'E)-7-bromoindirubin-3'-[O-(2-diethylaminoethyl)-oxime]hydrochloride (60)

$^1$H NMR (DMSO, 400 MHz, δ ppm, J in Hz) 11.82 (1H, s, N'—H), 11.03 (1H, s, N—H), 10.52 (1H, brs, N'''—H), 8.58 (1H, d, J=8.0 Hz, H-4), 8.23 (1H, d, J=7.9 Hz, H-4'), 7.48 (2H, m, H-6', 7'), 7.35 (1H, d, J=8.0 Hz, H-6), 7.07 (1H, ddd, J=7.9, 5.4, 2.9 Hz, H-5'), 7.00 (1H, t, J=8.0 Hz, H-5), 5.03 (2H, t, J=6.1 Hz, H-1''), 3.68 (2H, t, J=6.1 Hz, H-2''), 3.25 (4H, m, N'''($CH_2CH_3$)$_2$), 1.22 (6H, t, J=7.1 Hz, N'''($CH_2CH_3$)$_2$); Anal. ($C_{21}H_{28}N_4O_2BrCl$) C, H, N.

Data for (2'Z,3'E)-1-methyl-7-bromoindirubin-3'-[O-(2-diethylaminoethyl)-oxime](61)

Yield: 88%; $^1$H NMR (DMSO, 400 MHz, δ ppm, J in Hz) 11.94 (1H, s, N'—H), 8.80 (1H, d, J=7.9 Hz, H-4), 8.17 (1H, d, J=7.8 Hz, H-4'), 7.46 (2H, m, 7'), 7.37 (1H, d, J=7.9 Hz, H-6), 7.07 (1H, ddd, J=7.8, 5.1, 3.1 Hz, H-5'), 6.95 (1H, t, J=7.9 Hz, H-5), 4.65 (2H, t, J=6.1 Hz, H-1''), 3.67 (3H, s, N—$CH_3$), 2.94 (2H, t, J=6.1 Hz, H-2''), 2.58 (4H, q, J=7.1 Hz, N'''($CH_2CH_3$)$_2$), 0.98 (6H, t, J=7.1 Hz, N'''($CH_2CH_3$)$_2$); CI-MS m/z 475, 477 (M+H)$^+$. Anal. ($C_{23}H_{31}N_4O_2Br$) C, H, N.

Data for (2'Z,3'E)-1-methyl-7-bromoindirubin-3'-[O-(2-diethylaminoethyl)-oxime]hydrochloride (62)

$^1$H NMR (DMSO, 400 MHz, δ ppm, J in Hz) 11.93 (1H, s, N'—H), 9.95 (1H, brs, N'''—H), 8.72 (1H, d, J=8.0 Hz, H-4), 8.22 (1H, d, J=7.8 Hz, H-4'), 7.49 (2H, m, H-6', 7'), 7.41 (1H, d, J=8.0 Hz, H-6), 7.08 (1H, ddd, J=7.8, 4.0, 1.5 Hz, H-5'), 7.02 (1H, t, J=8.0 Hz, H-5), 5.00 (2H, t, J=6.1 Hz, H-1''), 3.68 (5H, m, N—$CH_3$, H-2''), 3.26 (4H, m, N'''($CH_2CH_3$)$_2$), 1.21 (6H, t, J=7.3 Hz, N'''($CH_2CH_3$)$_2$); Anal. ($C_{22}H_{30}H_4O_2BrCl$) C, H, N.

Protein Kinase Assays

Biochemical Reagents

Sodium ortho-vanadate, EGTA, EDTA, Mops, β-glycerophosphate, phenylphosphate, sodium fluoride, dithiothreitol (DTT), glutathione-agarose, glutathione, bovine serum albumin (BSA), nitrophenylphosphate, leupeptin, aprotinin, pepstatin, soybean trypsin inhibitor, benzamidine, histone H1 (type III-S) were obtained from Sigma Chemicals. [γ-$^{33}$P]-ATP was obtained from Amersham. The GS-1 peptide (YR-RAAVPPSPSLSRHSSPHQSpEDEEE) was synthesized by the Peptide Synthesis Unit, Institute of Biomolecular Sciences, University of Southampton, Southampton SO16 7PX, U.K.

Buffers

Homogenization Buffer: 60 mM β-glycerophosphate, 15 mM p-nitrophenylphosphate, 25 mM Mops (pH 7.2), 15 mM EGTA, 15 mM $MgCl_2$, 1 mM DTT, 1 mM sodium vanadate, 1 mM NaF, 1 mM phenylphosphate, 10 μg leupeptin/ml, 10 μg aprotinin/ml, 10 μg soybean trypsin inhibitor/ml and 100 μM benzamidine.

Buffer A: 10 mM $MgCl_2$, 1 mM EGTA, 1 mM DTT, 25 mM Tris-HCl pH 7.5, 50 μg heparin/ml.

Buffer C: homogenization buffer but 5 mM EGTA, no NaF and no protease inhibitors.

Kinase Preparations and Assays

Kinase activities were assayed in Buffer A or C, at 30° C., at a final ATP concentration of 15 μM. Blank values were subtracted and activities calculated as pmoles of phosphate incorporated for a 10 min. incubation. The activities are usually expressed in % of the maximal activity, i.e. in the absence of inhibitors. Controls were performed with appropriate dilutions of dimethylsulfoxide.

CDK1/cyclin B was extracted in homogenization buffer from M phase starfish (*Marthasterias glacialis*) oocytes and purified by affinity chromatography on p9$^{CKShs1}$-sepharose beads, from which it was eluted by free p9$^{CKSshs1}$ as previously described (Meijer et al., 1997). The kinase activity was assayed in buffer C, with 1 mg histone H1/ml, in the presence of 15 μM [γ-$^{33}$P] ATP (3,000 Ci/mmol; 10 mCi/ml) in a final volume of 30 μl. After 30 min. incubation at 30° C., 25 μl aliquots of supernatant were spotted onto 2.5×3 cm pieces of Whatman P81 phosphocellulose paper, and, 20 sec. later, the filters were washed five times (for at least 5 mM. each time) in a solution of 10 ml phosphoric acid/liter of water. The wet filters were counted in the presence of 1 ml ACS (Amersham) scintillation fluid.

CDK5/p25 was reconstituted by mixing equal amounts of recombinant mammalian CDK5 and p25 expressed in *E. coli* as GST (glutathione-S-transferase) fusion proteins and purified by affinity chromatography on glutathione-agarose (p25 is a truncated version of p35, the 35 kDa CDK5 activator). Its activity was assayed with histone H1 in buffer C as described for CDK1/cyclin B.

GSK-3α/β was purified from porcine brain by affinity chromatography on immobilized axin (Meijer et al., 2003). It was assayed, following a 1/100 dilution in 1 mg BSA/ml 10 mM DTT, with 5 µl 4 µM GS-1 peptide substrate, in buffer A, in the presence of 15 µM [γ-$^{33}$P] ATP (3,000 Ci/mmol; 10 mCi/ml) in a final volume of 30 µl. After 30 min. incubation at 30° C., 25 µl aliquots of supernatant were processed as described above.

ProOinase protein kinase assays. All protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity and identity of each kinase was checked by SDS-PAGE/Coomassie staining and by Western blot analysis. A proprietary protein kinase assay ($^{33}$ PanQinase® Activity Assay) was used to assay the recombinant enzymes. All kinase assays were performed in 96-well FlashPlates™ from Perkin Elmer/NEN (Boston, Mass., USA) in a 50 µl reaction volume using a BeckmanCoulter/Sagian robotic system. The reaction cocktail was pipetted in four steps in the following order: (i) 20 µl of assay buffer, (ii) 5 µl of ATP solution (in $H_2O$), (iii) 5 µl of test compound (in 10% DMSO) and (iv) 10 µl of substrate/10 µl of enzyme solution (premixed). The assays for all kinases (except for PKC, see below) contained 60 mM HEPES-NaOH, pH 7.5, 3 mM $MgCl_2$, 3 mM $MnCl_2$, 3 µM Na-orthovanadate, 1.2 mM DTT, 50 µg/ml $PEG_{20000}$, 1 µM [γ-$^{33}$P]-ATP (approx. $5\times10^5$ cpm per well). The final DMSO concentration was 1% in all assays. PKC assays contained 60 mM HEPES-NaOH, pH 7.5, 1 mM EDTA, 1.25 mM EGTA, 5 mM $MgCl_2$, 1.32 mM $CaCl_2$, 5 µg/ml phosphatidylserine, 1 µg/ml 1.2 dioleyl-glycerol, 1.2 mM DTT, 50 µg/ml $PEG_{20000}$, 1 µM [γ-$^{33}$P]-ATP (approx. $5\times10^{05}$ cpm per well). The reaction cocktails were incubated at 30° C. for 80 minutes. The reaction was stopped with 50 µl of 2% (v/v) $H_3PO_4$, plates were aspirated and washed two times with 200 µl $H_2O$ or 200 µl 0.9% (w/v) NaCl. Incorporation of $^{33}P_i$ was determined with a microplate scintillation counter (Microbeta, Wallac). With the residual activities (in %) obtained for each concentration the compound $IC_{50}$ values were calculated using Prism 3.03 for Windows (Graphpad, San Diego, Calif., USA). The model used was "sigmoidal response (variable slope)" with parameters "top" fixed at 100% and "bottom" at 0%.

Cell Biology

Chemicals and Antibodies

BisBenzimide (Hoechst 33342) and propidium iodide were obtained from Sigma Chemicals. AcDEVDafc and Q-VD-OPh was purchased from MPbiomedicals (Vannes, France). Cell Titer 96® kit containing the MTS reagent was purchased from Promega (Madison, Wis., USA). 2,3,7,8-tetrachlorodibenzo-p-dioxin (TCDD) was obtain from Dr. Steve Safe (Veterinary Physiology and Pharmacology, Texas A&M University, College Station, Tex. 77843, USA). The protease inhibitor cocktail was from Roche. IFN-α was obtained from R and D systems and all-trans-Retinoic Acid (RA), from Tocris (Bristol, UK). Unless otherwise stated, the non-listed reagents were also from Sigma.

Monoclonal antibodies against $p21^{WAF1/CIP1}$ and actin were obtained from Oncogene. Antibodies against $p27^{KIP1}$ and p53 were purchased from Santa Cruz Biotechnology. Monoclonal antibody against cytochrome C and rabbit polyclonal against Bcl-XL were provided by BD Biosciences. AntiBcl-2 (clone 124) monoclonal antibody was purchased from DAKO. Anti-PhosphoTyr705-STAT3 and anti-STAT3 antibodies were from Cell Signalling. The anti-tubulin antibody was from Sigma.

Cell Lines and Culture Conditions

The mouse 5 L hepatoma cell line (AhR+/+) and BP8 (an AhR−/− subclone) were obtained from by Dr. M. Goëttlicher (Forschungszentrum Karlsruhe, Institute of Genetics, 76021 Karlsruhe, Germany). They were cultured in Dulbecco's modified Eagle medium (DMEM) (Biowhittaker) supplemented with 2 mM L-glutamine (Eurobio), 10% fetal calf serum (FCS), and gentamycin (Gibco BRL) at 37° C. in an atmosphere of 7% $CO_2$. Indirubin or TCDD treatments were performed on 50-60% confluent cultures at the indicated time and concentrations. Control experiments were carried out using appropriate dilutions of DMSO.

SH-SY5Y, IMR-5 and IMR-32 human neuroblastoma cell lines were grown in DMEM medium from (Biowhittaker) plus 2 mM L-glutamine from Eurobio (Courtaboeuf, France) or DMEM already supplemented with 2 mM L-glutamine (Invitrogen, Barcelona, Spain), plus antibiotics and a 10% volume of FCS (Invitrogen, Cergy Pontoise, France or Barcelona, Spain). SH-SY5Y cell lines permanently transfected with pcDNA3/Bcl-2, pcDNA3/Bcl-XL and empty pcDNA3 vectors were grown like their untransfected counterparts. However, Geneticin (G-418) selection was maintained in the growing cultures before the terminal experiments (Ribas and Boix, 2004). In order to induce differentiation, SH-SY5Y cells were cultured on collagen coated plates and treated with 10 µM RA for five days.

HL-60 and Jurkat cells were grown in RPMI 1640 medium with 10% FCS and antibiotics from Invitrogen (Barcelona, Spain).

HCT116 human adenocarcinoma cell line were obtained from Dr. Vogelstein (The Howard Hughes Medical Institute, Sidney Kimmel Comprehensive Cancer Center, The Johns Hopkins School of Medicine, Baltimore, Md. 21231, USA). HCT116 cells were cultured in McCoy's 5A (Biowhittaker) supplemented with antibiotics and 10% FCS. General culture conditions were an atmosphere of 5% $CO_2$ and a temperature of 37° C. Culture dishes and other plastic disposable tools were supplied by Corning (Corning, N.Y., USA). Indirubin treatments were performed on exponentially growing cultures at the indicated time and concentrations. Control experiments were carried also using appropriate dilutions of DMSO.

MDA-MB-231 cells (derived from hormone-independent breast cancer) were cultured in DMEM supplemented with 10% FCS. For experiments, these cells were seeded in 24-well boxes or in 35 mm Petri dishes at appropriate densities ($4.10^4$ cells per well for cell growth experiments; $10^5$ cells per dish for cell cycle analysis) and exposed to indirubins as indicated.

Cell Proliferation and Cell Cycle Analysis

Propidium iodide (PI) staining was performed as follows. First, SH-SY5Y cells were harvested from the culture plates and washed once with PBS (Phosphate Buffered Saline, pH 7.4). Second, $1-2\times10^5$ cells were incubated for 15 min in 25 µg/ml propidium iodide, 10 µg/ml RNase A, and 0.1% Triton X-100. Flow cytometry readings were obtained by an EPICS® XL unit from Coulter Cientifica, S A (Madrid, Spain). Data were processed by means of WinMDI (a free software from Joe Trotter) in order to obtain monoparametric DNA histograms. Finally, these histograms were analysed with the Multi-Cycle software.

Cell Death and Cell Viability Assessments

Cell death characterization based on nuclear morphology was assessed by double staining with 0.05 μg/ml bisBenzimide and 25 μg/ml propidium iodide. Cell viability was determined by means of the MTS method. Both procedures have been previously described in detail (Ribas and Boix, 2004). For evaluation of DNA laddering, cell DNA was extracted and electrophoresed in 1.5% agarose gels to evidence the internucleosomal fragmentation typical of apoptosis.

Caspase Assay

The measurement of caspase activity is based on determining the fluorescence released from the AcDEVDafc synthetic substrate after its direct addition to the culture medium, detergent lysis, and incubation at 37°. This method is devised to be applied to 96 multiwell plates. It allows kinetic determinations of caspase activation and the characterization of multiple drugs simultaneously. (Ribas et al., 2005).

Electrophoresis and Western blotting

Whole cell extracts were obtained in buffer containing 100 mM Tris/HCl pH. 6.8, 1 mM EDTA, 2% SDS. Following heat denaturation for 3 minutes, proteins were separated by 10% SDS-PAGE (0.7 mm thick gels) (p27$^{Kip1}$) or by 10% NuPAGE pre-cast Bis-Tris polyacrylamide mini gel electrophoresis system (Invitrogen) with MOPS SDS (p53, p21$^{CiP1}$, actin) or MES SDS (cytochrome C) running buffer depending on protein size. Proteins were transferred to 0.45 μm nitrocellulose filters (Schleicher and Schuell). These were blocked with 5% low fat milk in Tris-Buffered Saline-Tween-20, incubated for 1 h with antibodies (anti-p27$^{KIP1}$: 1:1000; anti-actin: 1:1000; anti-Bcl-2, 1.2000; anti-Bcl-XL, 1:5000; anti-tubulin, 1:4000; anti-STAT3: 1:1000) or overnight at 4° C. (anti-p53: 1:1000; p21$^{Cip1}$: 1:1000; cytochrome C: 1:1000; anti-actin: 1:5000 (STAT3 experiment); anti-phospho-Tyr705-STAT3: 1:1000) and analyzed by Enhanced Chemiluminescence (ECL, Amersham).

To study expression of p53 and p21$^{Cip1}$, cells were lysed for 30 minutes at 4° C. in RIPA buffer (150 mM NaCl, 1% NP40, 0.5% deoxycholate, 0.1% SDS and 50 mM Tris-HCl pH 8.0) supplemented with a protease inhibitor cocktail (Roche). After centrifugation (12000 g for 10 minutes), the protein concentration was determined in the supernatants by the Bradford protein assay (Bio-Rad). To study cytochrome C release from mitochondria, a 0.05% digitonin cytosolic extraction was performed (Ribas and Boix, 2004).

In the STAT3 study, cells were lyzed in 30 mM HEPES (pH 7.5), 10 mM NaCl, 5 mM MgCl$_2$, 25 mM NaF, 1 mM EGTA, 1% Triton X-100, 10% glycerol, 2 mM sodium orthovanadate, 6.4 mg/mL p-nitrophenylphosphate and protease inhibitor cocktail (Roche). 73 μg of total proteins was resolved on 10% NuPAGE with MOPS SDS running buffer.

RESULTS

Molecular Modeling of 7-BIO in the ATP-Binding Pocked of Kinases

7BIO was modeled into GSK-3 and PfPK5 based on the co-crystal structures of indirubins with these kinases.

As shown on FIG. 1, a steric hindrance would prevent 7-BIO from interacting with classical kinases targets of other indirubins such a CDKs and GSK-3.

Effects of Indirubins of the Invention on Kinases

Results concerning various 7-halogeno-substituted indirubins (compounds 7-38) was on three protein kinases and on the survival of neuroblastoma SH-SY5Y cells are given hereinafter in Table 1.

Results obtained with indirubins which are not substituted on position 7 are also given for comparison purposes (compounds 1-6).

Molecules were then tested on three kinases, CDK1/cyclin B, CDK5/p25 and GSK-3α/β.

IC$_{50}$ values were calculated from the dose-response curves and are reported in μM. The compounds were also tested at 25 μM for their effects on SH-SY5Y cells.

Cell survival was estimated by the MTS reduction assay and is expressed in % of survival in untreated cells (average±s.e. of three independent measurements; representative of two independent experiments) (underlined in black for ≤15% survival, in grey for ≤50% survival).

TABLE 1

| Indirubin | R (3') | X (7) | Z (1) | CDK1 (IC$_{50}$) | CDK5 (IC$_{50}$) | GSK-3 (IC$_{50}$) | SH-SY5Y (% survival) |
|---|---|---|---|---|---|---|---|
| 1 | O | H | H | 10 | 10 | 1.0 | 104 ± 4 |
| 2 | NOH | H | H | 0.18 | 0.10 | 0.022 | 27 ± 2 |
| 3 | NOCH3 | H | H | 1.4 | 0.4 | 0.3 | 86 ± 4 |
| 4 | NOCOCH3 | H | H | 1.2 | 0.7 | 0.2 | 36 ± 2 |
| 5 | O | H | CH3 | 100 | >100 | >100 | 98 ± 3 |
| 6 | NOH | H | CH3 | 73 | >100 | >100 | 100 ± 5 |
| 7 | O | F | H | 10 | ≥10 | 0.40 | 70 ± 5 |
| 8 | NOH | F | H | 1.5 | 0.51 | 0.27 | 46 ± 2 |
| 9 | NOCH3 | F | H | >10 | >100 | 0.44 | 105 ± 4 |
| 10 | NOCOCH3 | F | H | 15 | >100 | 0.33 | 39 ± 4 |
| 11 | O | F | CH3 | >10 | >100 | >100 | 101 ± 7 |
| 12 | NOH | F | CH3 | >100 | >100 | >100 | 99 ± 1 |
| 13 | NOCH3 | F | CH3 | >10 | >100 | >100 | 107 ± 3 |
| 14 | NOCOCH3 | F | CH3 | >10 | >100 | >100 | 105 ± 4 |
| 15 | O | Cl | H | >10 | >100 | >100 | 92 ± 1 |
| 16 | NOH | Cl | H | 3.7 | 6 | 21 | 7 ± 0 |
| 17 | NOCH3 | Cl | H | >10 | >100 | >100 | 97 ± 2 |
| 18 | NOCOCH3 | Cl | H | >10 | >100 | >100 | 89 ± 3 |
| 19 | O | Cl | CH3 | >10 | >100 | >100 | 94 ± 5 |

TABLE 1-continued

| | | | | | | | |
|---|---|---|---|---|---|---|---|
| 20 | NOH | Cl | CH3 | >100 | >100 | >100 | 94 ± 2 |
| 21 | NOCH3 | Cl | CH3 | >10 | >100 | >100 | 99 ± 2 |
| 22 | NOCOCH3 | Cl | CH3 | >10 | >100 | >100 | 96 ± 1 |
| 23 | O | Br | H | >100 | >100 | >100 | 92 ± 1 |
| 24 | NOH | Br | H | 22 | 33 | 32 | 4 ± 0 |
| 25 | NOCH3 | Br | H | >100 | >100 | >100 | 97 ± 3 |
| 26 | NOCOCH3 | Br | H | >100 | >100 | >100 | 61 ± 8 |
| 27 | O | Br | H | 100 | >100 | >100 | 98 ± 3 |
| 28 | NOH | Br | CH3 | >100 | >100 | >100 | 84 ± 2 |
| 29 | NOCH3 | Br | CH3 | >100 | >100 | >100 | 100 ± 2 |
| 30 | NOCOCH3 | Br | CH3 | 70 | >100 | >100 | 95 ± 1 |
| 31 | O | I | H | >10 | >100 | >100 | 96 ± 2 |
| 32 | NOH | I | H | 66 | 77 | 16 | 64 ± 3 |
| 33 | NOCH3 | I | H | >10 | >100 | >100 | 84 ± 3 |
| 34 | NOCOCH3 | I | H | >10 | >100 | >100 | 67 ± 2 |
| 35 | O | I | CH3 | >10 | >100 | >100 | 93 ± 2 |
| 36 | NOH | I | CH3 | >100 | >100 | 30 | 74 ± 0 |
| 37 | NOCH3 | I | CH3 | >10 | >100 | >100 | 99 ± 2 |
| 38 | NOCOCH3 | I | CH3 | >10 | >100 | >100 | 82 ± 2 |

A complete lack of activity was confirmed for all N1-methylated indirubins. A weak and gradually decreasing inhibitory activity was observed with 7-halogeno-indirubin-3'-oxime when the size of the atom at position 7 increased (H>F>Cl>Br>I) (compare compounds 2, 8, 16, 24, 32), suggesting increased hindrance at this position 7.

In a second series of indirubins, the 3' substituent was varied on a 7-bromo-indirubin scaffold (±a methyl at N1) (compounds 39-68).

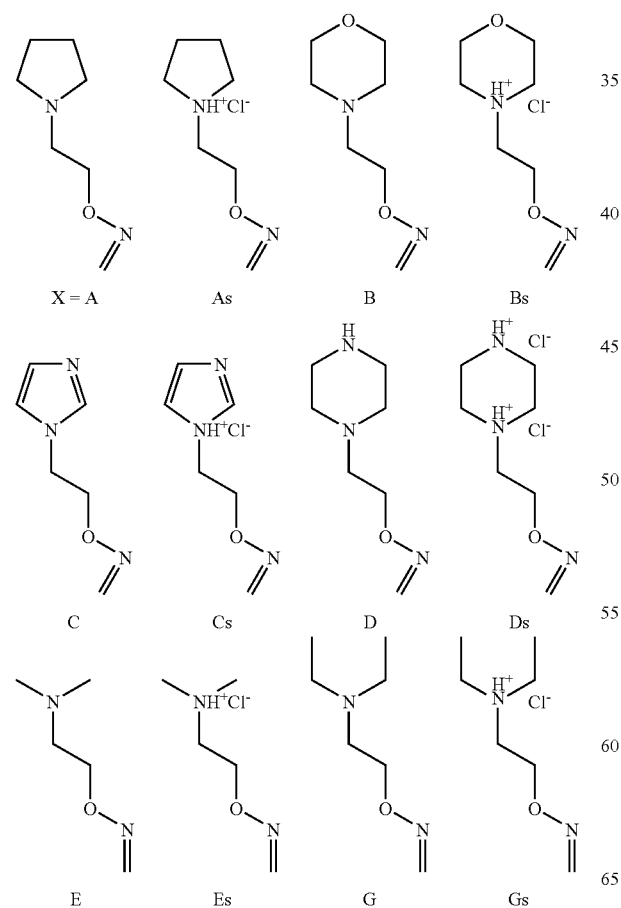

-continued

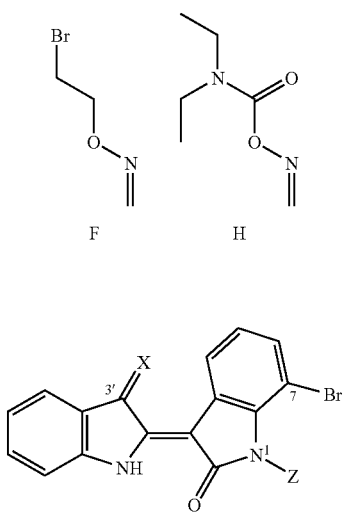

The results are given in table 2.

TABLE 2

| Indirubin | R (3') | Z (1) | CDK1 (IC$_{50}$) | CDK5 (IC$_{50}$) | GSK3 (IC$_{50}$) | SH-SY5Y (% survival) |
|---|---|---|---|---|---|---|
| 24 | NOH | H | 22 | 33 | 32 | 4 ± 0 |
| 39 | A | H | >100 | >10 | 7 | 13 ± 0 |
| 40 | As | H | >100 | >10 | 3 | 12 ± 0 |
| 41 | A | CH3 | >10 | >10 | >10 | 15 ± 1 |
| 42 | As | CH3 | >10 | >10 | >10 | 1 ± 0 |
| 43 | B | H | >100 | >10 | 0.57 | 98 ± 1 |
| 44 | Bs | H | >100 | >10 | >100 | 76 ± 1 |
| 45 | B | CH3 | >10 | >10 | >10 | 98 ± 2 |
| 46 | Bs | CH3 | >10 | >10 | >10 | 90 ± 2 |
| 47 | C | H | >10 | >10 | 9 | 59 ± 1 |
| 48 | Cs | H | >10 | >10 | 11 | 62 ± 1 |
| 49 | C | CH3 | >10 | >10 | >10 | 85 ± 1 |

TABLE 2-continued

| 50 | Cs | CH3 | >10 | >10 | >10 | 70 ± 1 |
| 51 | D | H | >10 | >10 | 5 | 3 ± 1 |
| 52 | Ds | H | >10 | >10 | >10 | 3 ± 1 |
| 53 | E | H | >10 | >10 | 8 | 1 ± 0 |
| 54 | Es | H | >10 | >10 | >10 | 5 ± 1 |
| 55 | E | CH3 | >10 | >10 | >10 | 49 ± 1 |
| 56 | Es | CH3 | >10 | >10 | >10 | 4 ± 0 |
| 57 | F | H | >100 | 25 | 100 | 87 ± 5 |
| 58 | F | CH3 | >10 | >10 | >10 | 99 ± 4 |
| 59 | G | H | >10 | >10 | >10 | 49 ± 3 |
| 60 | Gs | H | >10 | >10 | >10 | 72 ± 3 |
| 61 | G | CH3 | >10 | >10 | >10 | 83 ± 2 |
| 62 | Gs | CH3 | >10 | >10 | >10 | 15 ± 1 |
| 63 | H | H | >100 | >100 | >100 | 106 ± 5 |
| 64 | H | CH3 | >10 | >10 | >10 | 105 ± 3 |
| 5BIO | NOH | H | 0.045 | 0.028 | 0.016 | 13 ± 0.4 |
| 6BIO | NOH | H | 0.320 | 0.083 | 0.005 | 5 ± 0.6 |

With the exception of compound 43 on GSK-3, none of these compounds displayed any significant activity on any of the three kinases tested.

Effect of 3'-, 7-Substituted Indirubins on Cell Death in Culture

The effects of each indirubin was tested, at a 25 μM final concentration, on the survival of the neuroblastoma SH-SY5Y cell line after 24 h or 48 h exposure. Cell survival was estimated by the MTS reduction assay.

Experiments were also performed with 5BIO and 6BIO, for comparison.

$IC_{50}$ values were calculated from the dose-response curves and are reported in μM (average±s.e. of two independent measurements performed in triplicates) (underlined in grey for $IC_{50}$<10 μM).

In addition, cell death was estimated 48 h after the addition of each indirubin (25 μM) using the LDH release assay.

Results are expressed as % cell death (underlined in black for >85% cell death, in grey for >50% cell death).

Several compounds showed clear effects on the SH-SY5Y cell survival rate.

A complete dose-response curve was performed for these active compounds and the $IC_{50}$ values were calculated. The results are given in table 3 and illustrated by FIG. 2.

TABLE 3

| Indirubin | cell survival ($IC_{50}$) (MTS reduction) | | % cell death (LDH release) |
|---|---|---|---|
| | (24 h) | (48 h) | (48 h) |
| 2 | >25 | 12 | 33 |
| 16 | 14 | 12 | 92 |
| 24 (7BIO) | 8.0 | 7.1 | 94 |
| 39 | 3.6 | 2.3 | 14 |
| 40 | 3.1 | 2.0 | 80 |
| 41 | 7.8 | 5.0 | 78 |
| 42 | 7.3 | 4.0 | 94 |
| 51 | 10.5 | 6.2 | 94 |
| 52 | 6.0 | 6.0 | 100 |
| 53 | 4.1 | 2.0 | 86 |
| 54 | 2.1 | 1.0 | 84 |
| 55 | >25 | 5.5 | 33 |
| 56 | 21 | 9.0 | 80 |
| 62 | 23 | 18 | 58 |
| 5BIO | 18 | 12 | 59 |
| 6BIO | 18 | 9.5 | 80 |

As MTS reduction is occasionally observed under conditions different from cell death, an independent cell death evaluation procedure was used, the lactate dehydrogenase (LDH) release assay. This assay confirmed the induction of cell death by the indirubins of the invention, despite their overall lack of effects on CDKs and GSK-3.

Effects of 3'-Substituted, 7-Bromoindirubins on the Survival of Cell Lines

The effects of 3'-, 7-bromo indirubins on eleven other cell lines, namely HT-29 and HCT116 (colon cancer), MDA-MB-231 (breast cancer), A549 (lung cancer), PC3 (prostate cancer), 5 L and BP8 (hepatoma), F1 and Huh7 (hepatoma), SH-SY5Y (neuroblastoma) and HEK293 (embryonic kidney) are reported hereinafter. Like SH-SY5Y, these cell lines showed dose-dependent induction of cell death (Table 4), suggesting the generality of effect of these compounds on cell survival rather than a cell type or differentiation stage-specific effect. The similar sensitivity of 5 L (AhR+/+) and BPS (AhR-/-) suggests that AhR does not play a major role in 3'-, 7-bromo indirubins—induced cell death.

Cell survival was estimated 48 h after the addition of each indirubin using the MTS reduction assay. Experiments were also performed with 5BIO and 6BIO, for comparison. $IC_{50}$ values were calculated from the dose-response curves and are reported in μM (average±s.e. of measurements performed in triplicates) (underlined in grey for $IC_{50}$<10 μM, in black for $IC_{50}$<1 μM).

Like SH-SY5Y, these 11 cell lines showed dose-dependent induction of cell death. The results are given in table 4.

TABLE 4

| Cell line | Cell survival ($IC_{50}$, μM) (MTS reduction assay) | | | | | | | | |
|---|---|---|---|---|---|---|---|---|---|
| | 24 | 40 | 41 | 42 | 51 | 52 | 53 | 54 | 56 |
| HT-29 (colon) | 21.2 | 10.4 | 19.8 | 5.4 | 6.3 | 1.9 | 21.8 | 2.4 | 0.0 |
| HCT116 (colon) | 6.2 | 3.8 | 13.6 | 5.1 | 5.4 | 5.1 | 6.5 | 2.0 | 5.7 |
| MDA-MB-231 (breast) | 10.5 | >30.0 | 26.8 | 12.0 | 5.3 | 5.1 | 26.4 | 18.8 | 7.8 |
| A549 (lung) | 21.8 | 16.0 | 21.0 | 14.6 | 5.9 | 6.0 | 21.8 | 5.8 | 0.8 |
| PC3 (prostate) | 19.8 | 30.0 | 21.6 | 19.0 | 6.1 | 6.0 | 27.2 | 15.0 | 5.0 |
| 5L (hepatoma) | 20.0 | >30.0 | 18.8 | 13.0 | 5.2 | 5.4 | 25.0 | >30.0 | 4.0 |
| BP8 (hepatoma) | 19.4 | >30.0 | 18.8 | 7.5 | 5.6 | 5.4 | 19.5 | >30.0 | 9.0 |
| F1 (hepatoma) | 8.0 | 3.1 | 5.6 | 2.9 | 1.7 | 1.4 | 5.5 | 1.7 | .4 |
| Huh7 (hepatoma) | 9.0 | 13.6 | 18.8 | 5.6 | 5.3 | 2.0 | 19.6 | 11.2 | 8.0 |
| SH-SY5Y (neuroblastoma) | 7.4 | 2.1 | 10.6 | 5.0 | 5.4 | 5.1 | 5.4 | 0.8 | .0 |
| HEK293 (embryo kidney) | 12.3 | >30.0 | 21.4 | 8.0 | 5.0 | 1.9 | 14.4 | 3.0 | 8.8 |

The results show the generality of effect of these compounds on cell survival rather than a cell type or differentiation stage-specific effect.

3'-,7-Substituted Indirubins Induce Apoptotic and Non-Apoptotic Cell Death

The inventors showed that cell death induced by 7BIO is primarily different from apoptosis as it does not induce nor require caspase activation. The effects of the general effector caspase inhibitor Q-VD-OPh (Caserta et al., 2003) (20 µM final concentration) on cell death induced by the selection of indirubins was tested to investigate whether the 3'-, 7-substituted indirubins of the invention induce or require caspase activation.

SH-SY5Y cells were treated with various concentrations of indirubin analogues in the presence or absence of 20 µM Q-VD-OPh, a broad spectrum inhibitor of caspases.

Cell survival was estimated 43 h after the addition of each indirubin using the MTS reduction assay.

$IC_{50}$ values were calculated from the dose-response curves and are reported in µM (average±s.e. of two independent measurements), no cell death at highest concentration tested.

Results are not underlined when Q-VD-Oph has no effect on the dose-response curve, in grey when Q-VD-Oph partially protects from cell death, and in black when Q-VD-Oph provides complete protection.

The results are given in Table 5 and illustrated by FIG. 2.

TABLE 5

| Indirubin | -Q-VD-OPh (MTS) | +Q-VD-OPh (MTS) |
|---|---|---|
| 2 | 13.0 | >25.0 |
| 16 | 10.0 | 11.0 |
| 24 (7BIO) | 7.0 | 7.0 |
| 39 | 2.0 | -(>25.0) |
| 40 | 2.8 | -(>25.0) |
| 41 | 6.1 | >25.0 |
| 42 | 5.0 | 13.0 |
| 51 | 10.0 | 10.3 |
| 52 | 6.2 | 6.8 |
| 53 | 1.5 | -(>25.0) |
| 54 | 1.1 | -(>25.0) |
| 55 | 6.4 | -(>25.0) |
| 56 | 11.0 | >25.0 |
| 62 | 18.0 | >25.0 |
| 5BIO | 13.0 | 23.0 |
| 6BIO | 10.0 | 13.0 |

Results show that 3'-substituted 7-bromoindirubins fall in three categories.

In the first category, some indirubins are completely insensitive to the presence of the caspase inhibitor, suggesting a caspase-independent mechanism. 7BIO falls in this category.

In contrast to its 5-bromo-(5BIO) and 6-bromo-isomers, and to indirubin-3'-oxime, 7BIO has only a marginal inhibitory activity towards CDKs and GSK-3 (Table 6). We have investigated the selectivity of IO, 5BIO, 6BIO and 7BIO in the 85 kinase ProQinase selectivity panel (Table 7) This approach first revealed that Aurora A-C, FLT3, RET constitute new targets of IO, 5BIO and 6BIO. VEGF-R had been described as a target for indirubins (Jautelat et al., 2005). The selectivity panel revealed that, compared to the three other indirubins, 7BIO is a poor kinase inhibitor.

TABLE 6

| | X | Y | Z | |
|---|---|---|---|---|
| 1 | H | H | H | (IO) |
| 2 | Br | H | H | (5BIO) |
| 3 | H | Br | H | (6BIO) |
| 4 | H | H | Br | (7BIO) |
| 5 | H | H | Cl | (7ClO) |
| 6 | H | H | I | (7IIO) |
| 7 | H | H | F | (7FIO) |

8 Me7BIO

| N° | Compound | GSK-3 α/β | CDK1/ cyclin B | CDK5/ p25 |
|---|---|---|---|---|
| 1 | indirubin-3'-oxime (IO) | 0.022 | 0.180 | 0.100 |
| 2 | 5-bromoindirubin-3'-oxime (5BIO) | 0.016 | 0.045 | 0.028 |
| 3 | 6-bromoindirubin-3'-oxime (6BIO) | 0.005 | 0.320 | 0.083 |
| 4 | 7-bromoindirubin-3'-oxime (7BIO) | 32 | 22 | 33 |
| 5 | 7-chloroindirubin-3'-oxime (7ClO) | 21 | 3.7 | 6 |
| 6 | 7-iodoindirubin-3'-oxime (7IIO) | 16 | 66 | 77 |
| 7 | 7-fluoroindirubin-3'-oxime (7FIO) | 0.270 | 1.5 | 0.510 |
| 8 | 1-methyl-7-bromoindirubin-3'-oxime (Me7BIO) | >100 | >100 | >100 |

($IC_{50}$ values in µM)

TABLE 7

Selectivity profile of IO, 5BIO, 6BIO and 7BIO.
The four indirubins were tested at various concentrations in 85 kinase assays, as described in the Material and Methods section. n.t., not tested. $IC_{50}$ values, calculated from the dose-response curves, are reported in μM and underlined according to a gray scale code:

| $IC_{50}$ value (μM) | <0.1 | 0.1-1 | 1-10 | 10-100 | >100 |
|---|---|---|---|---|---|

| KINASE | IO | 5BIO | 6BIO | 7BIO |
|---|---|---|---|---|
| ABL1 | >100 | >100 | 3.4 | >100 |
| AKT1 | >100 | >100 | >100 | >100 |
| AKT2 | >100 | >100 | >100 | >100 |
| AKT3 | n.t. | n.t. | >100 | >100 |
| Aurora-A |  |  |  | 55 |
| Aurora-B | 1.4 | 35 | 1.5 | 4.7 |
| Aurora-C |  | 34 | 2.3 | 6.6 |
| BRK | 17 | >100 | 4.6 | 33 |
| CDK1/CycB | 20 | 2.1 | 21 | >100 |
| CDK2/CycA | 2.3 |  |  | >100 |
| CDK2/CycE | 2.2 |  |  | >100 |
| CDK3/CycE |  |  | 0.04 | 0.07 | 
| CDK4/CycD1 |  | 1.35 |  | >100 |
| CDK6/CycD1 |  |  | 0.05 |  |
| CHK1 | 35 | >100 | 12 | >100 |
| CK2 | >100 | >100 | >100 | >100 |
| COT | n.t. | n.t. | 75 | 49 |
| CSK | >100 | >100 | n.t. | n.t. |
| DAPK1 | >100 | >100 | n.t. | n.t. |
| EGF-R | 102 | >100 | 9.1 | 27 |
| EPHA1 | 53 | >100 | 38 | 44 |
| EPHB1 | 56 | >100 | n.t. | n.t. |
| EPHB2 | 6.1 | >100 | 5.0 | 33 |
| EPHB3 | >100 | >100 | 34 | 28 |
| EPHB4 | 8.6 | >100 | 3.5 | 10.0 |
| ERBB2 | >100 | >100 | >100 | 26 |
| ERBB4 | >100 | >100 | >100 | >100 |
| FAK |  | >100 | 12 | 78 |
| FGF-R1 |  |  |  | 36 |
| FGF-R3 |  |  |  | 23 |
| FGF-R4 | 13 | 65 | 1.2 | 17 |
| FGR | 1.6 | >100 | 0.09 | 20 |
| FLT3 | 0.07 | 0.02 |  |  |
| GSK3-beta | 2.5 | 0.07 |  | >100 |
| IGF1-R | 5.3 | 5.6 | 79 | 26 |
| IKK-beta | >100 | >100 | >100 | >100 |
| INS-R | 6.6 | 4.3 | >100 | >100 |
| IRAK4 | 1.8 | 44 | 4.8 | 82 |
| JAK2 | 33 | >100 | >100 | >100 |
| JNK3 | 25 | >100 | n.t. | n.t. |
| KIT | 4.3 | 16 |  | 58 |
| LCK | 41 | >100 | 3.1 | >100 |
| MET | >100 | >100 | >100 | >100 |
| MST4 | 73 | >100 | n.t. | n.t. |
| MUSK |  | 31 |  | >100 |
| NEK2 | >100 | >100 | >100 | >100 |
| NEK6 | >100 | >100 | >100 | >100 |
| NLK | >100 | >100 | >100 | >100 |
| PAK1 | 13 | 11 | n.t. | n.t. |
| PAK2 | >100 | >100 | n.t. | n.t. |
| PAK4 | >100 | >100 | 91 | n.t. |
| PBK | >100 | >100 | >100 | >100 |
| PCTAIRE1 | >100 | >100 | >100 | >100 |
| PCTAIRE2 | n.t. | n.t. | 15 | >100 |
| PDGFR-alpha | 4.0 | 9.5 |  | 47 |
| PDGFR-beta | 3.4 | 3.4 |  | >100 |
| PIM1 | >100 | >100 | 91 | >100 |
| PIM2 | n.t. | n.t. | >100 | >100 |
| PKC-alpha | >100 | >100 | >100 | >100 |
| PKC-beta1 | >100 | >100 | >100 | >100 |
| PKC-beta2 | >100 | >100 | >100 | >100 |
| PKC-delta | >100 | >100 | >100 | 65 |
| PKC-epsilon | >100 | >100 | >100 | >100 |
| PKC-eta | >100 | >100 | >100 | >100 |
| PKC-gamma | >100 | >100 | >100 | >100 |
| PKC-iota | >100 | >100 | >100 | >100 |
| PKC-mu | >100 | >100 | >100 | >100 |

Unexpectedly, 7BIO triggers a rapid cell death process distinct from apoptosis. 7BIO induces the appearance of large pycnotic nuclei, without classical features of apoptosis such as chromatin condensation and nuclear fragmentation. 7BIO-induced cell death is not accompanied by cytochome C release nor by any measurable effector caspase activation. Furthermore it is not altered by the presence of Q-VD-OPh, a broad spectrum caspase inhibitor. Neither AhR nor p53 is required during 7BIO-induced cell death. Thus, in contrast to previously described indirubins, 7BIO triggers the activation of non-apoptotic cell death, possibly through necroptosis or autophagy.

In the second category, Q-VD-OPh shifts the dose-response curves to the right, thus the $IC_{50}$s towards higher values, suggesting a mixed, caspase-dependent and caspase-independent mechanism of action.

In the third category, the presence of Q-VD-OPh essentially protects cells from cell death, suggesting that these indirubins act mostly through a classical, caspase-dependent mechanise. Interestingly this is observed with the most active indirubins.

In this last category, a small fraction of cells (20%) die despite the presence of Q-VD-OPh.

Induction of Cell Death by Indirubins

Four indirubins IO, 5BIO, 6BIO, 7BIO were compared for their ability to induce cell death in neuroblastoma SH-SY5Y cells as measured with an MTS reduction assay (FIG. 3A). Since MTS reduction is occasionally observed under conditions different from cell death, an independent cell death assay was used, the lactate dehydrogenase (LDH) release assay (FIG. 3B). Dose-response curves showed that 7BIO is the most potent compound in terms of concentration required to reduce cell survival (MTS reduction) (FIG. 3A) or in terms of cell death (LDH release) (FIG. 3B). Different halogens were introduced in position 7 of indirubin-3'-oxime (FIG. 4, Table 6). 7FIO was poorly active on cells compared to the equipotent 7BIO and 7CIO. 7IIO was the most potent compound (FIG. 4A). These results did not correlate with those obtained in the in vitro kinase assays (Table 6). Methylation on N1, leading to Me7BIO, totally abolished the cell death inducing ability of 7BIO (FIG. 4B). As 7BIO was a poor inhibitor of kinases and yet a potent cell death inducer, the effects of this compound was investigated in more detail.

To ascertain that the induction of cell death by 7BIO was not a specific property of SH-SY5Y cells, the breast cancer cell line MDA-MB-231 was also used (FIG. 5). A 48 h exposure to 7BIO induced a dose-dependent inhibition of cell proliferation as evidenced by direct counting. This effect was poorly if at all reversible by removal of 7BIO (FIG. 5A). The effects of 7BIO on cell cycle distribution (FIG. 5B) were next analyzed. A tendency towards accumulation in G2/M and reduction of G0/G1 was observed, as previously described for other indirubins.

Induction of Cell Death by 7Bio does not Require AhR

Indirubins interact with AhR: This interaction may contribute to the cellular effects of indirubins. However SH-SY5Y cells seem to be devoid of AhR. To evaluate the contribution of AhR to the cell death effects of 7BIO two hepatoma cell lines, 5 L (AhR+/+) and its AhR-deficient sub-clone, BP8 (AhR−/−) were used. It was first confirmed that, like 2,3,7,8-tetrachlorodibenzo-p-dioxin (TCDD) (dioxin), both 7BIO and Me7BIO potently enhance the AhR-dependent expression of the CDK inhibitory protein p27$^{Kip1}$ (FIG. 6A), as previously reported for IO and 6BIO and their methylated counterparts, MeIO and Me6BIO. No correlation is thus observed between induction of p27$^{Kip1}$ expression (FIG. 6A) and induction of cell death (FIG. 4B). The effects of 7BIO and Me7BIO on cell cycle distribution of AhR−/− and AhR+/+ cells were next analyzed. As reported for other indirubins, both 7BIO and Me7BIO induced a striking AhR-dependent accumulation in G0/G1 (FIG. 6B). Finally cell death induction was estimated in both cell lines following exposure to increased 7BIO concentrations. The dose-response curves were essentially the same (FIG. 6C). Altogether these results show that AhR is not involved in the cell death inducing properties of 7BIO.

Induction of Cell Death by 7BIO is Much Faster than by Other Indirubins

A time-course of SH-SY5Y cell death induction was next performed following exposure to 25 µM IO, 5BIO, 6BIO, 7BIO or Me7BIO (FIG. 7). Although 5BIO and 6BIO required 36-48 h to induce 70% cell death, this level was reached by 12 h with 7BIO. Almost complete cell death was obtained with 7BIO within 24 h (FIG. 7). This much faster kinetics suggests that a different mechanism of cell death is occurring in the case of 7BIO compared to the other indirubins. Alternatively a sub-population of cells may respond to 5BIO and 6BIO as they do to 7BIO, while the vast majority undergoes apoptosis.

7BIO Induces Non-Apoptotic Cell Death

The mechanism of action of 7BIO was investigated by first examining under a fluorescence microscope, SH-SY5Y cells exposed to different indirubins following bisBenzimide and propidium iodide (PI) staining (FIG. 8). First of all, no PI staining was observed in control cells and in Me7BIO-treated cells (FIG. 8A, 8F), confirming the absence of cell death. IO, 5BIO and 6BIO all triggered nuclear fragmentation typical of apoptosis, accompanied by secondary necrosis (FIG. 8B-8D). These figures were never observed in 7BIO-treated cells which, in contrast, displayed numerous large, unfragmented pycnotic nuclei (FIG. 8E). Such figures were observed only occasionally with 5BIO and 6BIO (FIG. 8C-8D). These morphological results suggest that 7BIO triggers an atypical cell death different from apoptosis.

To challenge this possibility, the activity of caspases was assayed in SH-SY5Y cells exposed to various concentrations of different indirubins (FIG. 9). 5BIO and 6BIO, and IO to a lesser extent, triggered a dose-(FIG. 9A) and time (FIG. 9B) dependent activation of caspase activity. In sharp contrast, neither 7BIO nor Me7BIO induced any activation of caspases which remained at the level of control, untreated cells. Furthermore, Q-VD-Oph, a general caspase inhibitor, had no effect on cell death induced by 7BIO (FIG. 10), while it reduced the level of cell death induced by 5BIO and 6BIO, and IO, to a lesser extent (FIG. 10A). The time-course of 7BIO-induced cell death was unaffected by Q-VD-Oph (FIG. 10B).

Moreover, 7BIO triggered negligible release of cytochome C from mitochondria (FIG. 11). Under the same conditions IO, 5BIO and 6BIO induced the release of cytochome C to levels similar to those reached by standard apoptosis-inducing reagents like staurosporine and etoposide. DNA laddering as a reflection of apoptotic cell death was next examined. The laddering caused by R-Roscovitine was consistent with the reported ability of this compound to induce apoptosis (Ribas and Boix, 2004). 5BIO and to a lesser extent 6BIO, also induced internuclesosomal fragmentation, which intensity was proportional to the amount of apoptotic cells in the culture (see bisBenzimide/propidium iodide staining in FIG. 8). In 7BIO treated cells no ladder was observed, however most cells were dead. In Me7BIO, IO and DMSO treatments, cell death induction was negligible and no laddering was detected.

Altogether these results show that 7BIO-induced cell death does not induce cytochome C release and does not trigger nor require the activation of caspases, in sharp contrast with cell death induced by IO, 5BIO and 6BIO. Thus 7BIO appears to induce a cell death pathway which differs from the apoptosis induced by IO, 5BIO and 6BIO.

Figure 12A:
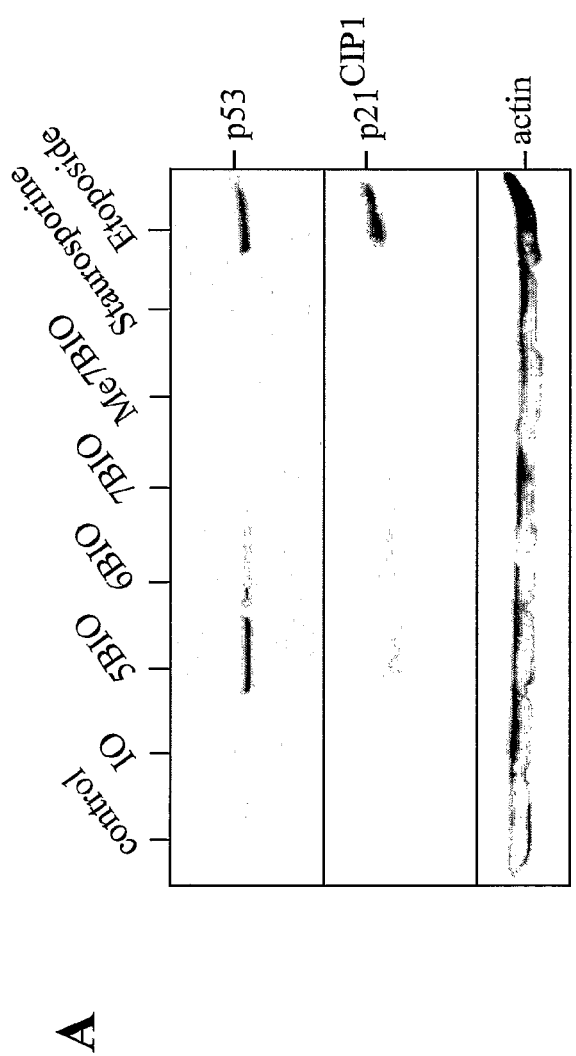
Figure 12E:
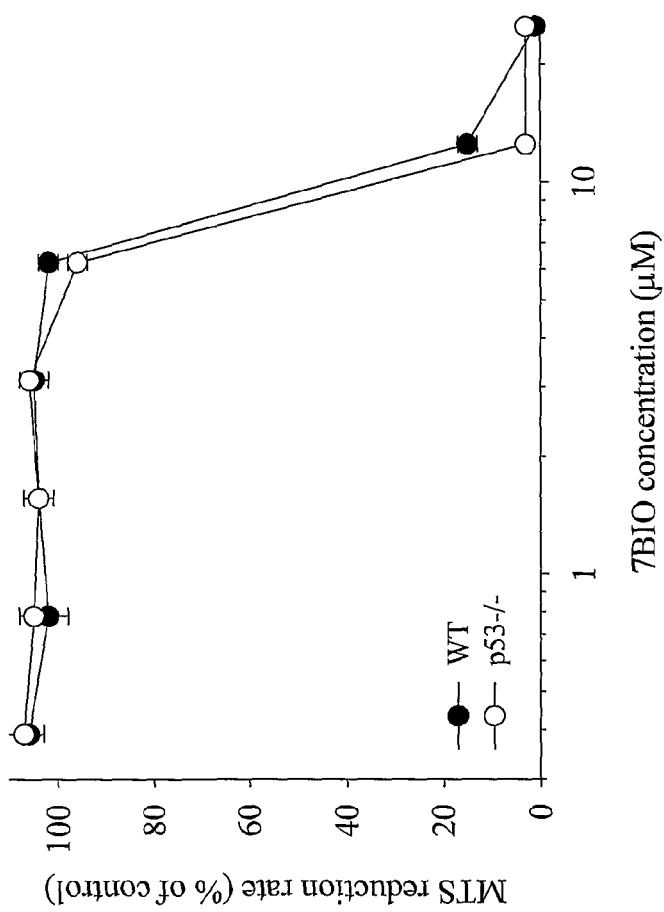

7BIO-Induced Cell Death Involves Neither p53 Nor p21$^{Cip1}$ Nor STAT3 Dephosphorylation The involvement of p53 and p21$^{Cip1}$ in cell death induced by the four indirubins (FIG. 12) was next investigated. P53 was strongly induced by 5BIO in a time-dependent manner in SH-SY5Y cells (FIG. 10A-B). Induction of p53 was only modest in cells treated with 6BIO and insignificant in cells treated with IO, 7BIO or Me7BIO (FIG. 12A-B). As expected analysis of p21$^{Cip1}$ expression under the same conditions showed a time-dependent induction by 5BIO (FIG. 12C). p21$^{Cip1}$ expression occurred with some delay after p53 stabilization (FIG. 10B). IO, 5BIO and 6BIO were roughly equipotent at inducing p21$^{Cip1}$ overexpression, while 7BIO and Me7BIO had negligible effects (FIG. 12A). Finally, we tested the effects of 7BIO on wild-type HCT-116 and HCT-116 sub-clones deprived of p53 (FIG. 12E). The dose-response curves were essentially the same. Altogether these data suggest that 7BIO-induced cell death does not induce p53 nor require its contribution.

Tyrosine phosphorylation and subsequent activation of the transcription factor STAT3 were recently shown to be inhibited by some indirubins, leading to the down-regulation of survival factors and subsequent induction of cell death. To examine whether this mechanism is involved in the action of 7BIO, the effect of IO, 5BIO, 6BIO and 7BIO on the level of tyrosine 705-phosphorylated STAT3 in MDA-MB-231 cells was investigated (FIG. 13). As a positive control, cells were also stimulated by interferon α (IFNα). Results show that the basal level of tyrosine 705-phosphorylated STAT3 MDA- MB-231 is very low compared to the level reached by stimulation with IFNα, yet it is down-regulated by IO, 5BIO and 6BIO but not by 7BIO. This suggests that the mechanism of action of 7BIO is not primarily due to an inactivation of tyrosine phosphorylated STAT3.

7BIO-Induced Cell Death is not Inhibited by Cellular Mechanisms Able to Protect Cells From Apoptosis.

To further explore the cell death process triggered by 7BIO, experiments were carried out to check if proved mechanisms of resistance to apoptosis were able to protect cells from 7BIO's effects. SH-SY5Y cells can be differentiated in cell culture by retinoic acid (RA) and this differentiation prevents apoptosis triggered by CDK inhibitors, like olomoucine or roscovitine (Ribas and Boix, 2004). Similarly, differentiation renders SH-SY5Y cells refractory to staurosporine (STS), an established agent used to induce canonical apoptosis. As shown in FIG. 14, differentiation had negligible effect on the rates of 7BIO-induced cell death.

Bcl-2 and Bcl-XL proteins are known for their anti-apoptotic effects. In addition, their cytoprotective effects have been found to extend beyond apoptosis (Kane et al, 1995). We previously described that Bcl-2 and Bcl-XL overexpression protects SH-SY5Y cells from apoptosis triggered by STS (Yuste et al., 2002). As reported, Bcl-XL surpassed Bcl-2 at inhibiting STS-induced apoptosis (FIG. 14B). However, in a parallel time course experiment, neither Bcl-XL nor Bcl-2 overexpression provided any significant protection from 7BIO (FIG. 14B). Taken together, these results reinforce the action of 7BIO as an effective cell killer acting in an apoptosis independent manner.

Non-Apoptotic, Caspase-Independent Cell Death is a General Characteristic of the Death Processes Triggered by 7BIO To challenge the generality of the 7BIO effects, 7BIO was tested in two other human neuroblastoma derived cell lines, IMR-5 and IMR-32, as well as two hematological tumors derived cell lines, Jurkat and HL-60. As shown in FIG. 15 (left column), 7BIO induced cell death in the same range of concentrations characterized as lethal for SH-SY5Y, MDA-MB-231 (breast cancer) and HCT116 (colon cancer) cell types. The sensitivity of HL-60 cells (known to be deficient in p53 protein) to 7BIO is consistent with the lack of involvement of p53 as described above.

The cell death process triggered by 7BIO in IMR-5, IMR-32, Jurkat and HL-60 cells was further characterized. Bisbenzimide staining, fluorescence and electron microcopy characterizations demonstrated that non-apoptotic cell death was taking place as described in SH-SY5Y cells. In addition, effector caspase activation was assessed at 24 h (FIG. 15, right). As expected, 5BIO triggered caspase activation. Compared with STS, 5BIO displayed reduced caspase activation, consistent with (1) the mixed type of cell death 5BIO induces and (2) less synchronous kinetics of apoptosis induction. In contrast DEVDase activity in 7BIO-treated cells fell consistently below the background displayed by control, untreated cells. In conclusion, the non-apoptotic, caspase-independent type of cell death triggered by 7BIO appears to be an intrinsic property of the compound, independent of cell model.

REFERENCES

Meijer L, Borgne A, Mulner O, Chong J P J, Blow J J, Inagaki N, Inagaki M, Delcros J G and Moulinoux J P. (1997). *Eur. J. Biochem.*, 243, 527-536.

Meijer L, Skaltsounis A L, Magiatis P, Polychonopoulos P, Knockaert M, Leost M, Ryan X P, Vonica C D, Brivanlou A, Dajani R, Tarricone A, Musacchio A, Roe, S M, Pearl L and Greengard P. (2003). *Chem. & Biol.*, 10, 1255-1266.

Ribas J Boix J. (2004). *Exp. Cell Res.*, 295, 9-24.

Ribas J, Gomez-Arbones X, Boix J. (2005). *Eur. J. Pharmacol.*, 524, 49-52.

Meijer L, Skaltsounis A L, Magiatis P, Polychonopoulos P, Knockaert M, Leost M, Ryan X P, Vonica C D, Brivanlou A, Dajani R, Tarricone A, Musacchio A, Roe, S M, Pearl L and Greengard P. (2003). *Chem. & Biol.*, 10, 1255-1266.

Polychonopoulos P, Magiatis P, Skaltsounis L, Myrianthopoulos V, Mikros E, Tarricone A, Musacchio A, Roe S M, Pearl L, Leost M, Greengard P and Meijer L. (2004). *J. Med. Chem.*, 47, 935-94.

The invention claimed is:

1. A 3'-, 7-substituted-indirubin of formula (I)

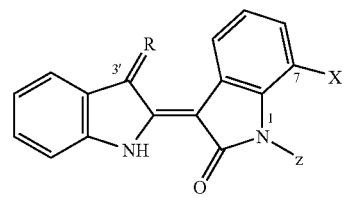

wherein R represents N—OH, N—O-alkyl, N—O—CO-alkyl, NO—$(R_a)_{n1}$-Het, N—O—$(Y)_{n1}$—$NR_aR_b$, or N—O—CO—N($R_b$, $R_c$), where $R_a$ and $R_b$ independently represent a $CH_2$— group or a $CH_3$— group, and $R_c$ represents a $CH_3$— group, and Het represents an aliphatic nitrogeneous heterocycle, Y being an optionally substituted —$CH_2$— radical, n1 being 1 to 3, and X is an halogen atom selected in the group comprising F, Cl, Br, and I, and Z is H or $CH_3$, or a salt thereof.

2. An Indirubin derivative according to claim 1, wherein R represents N—OH.

3. An Indirubin derivative according to claim 1, wherein R represents a N—O-alkyl radical.

4. A 3'-, 7-substituted-indirubin of formula (I)

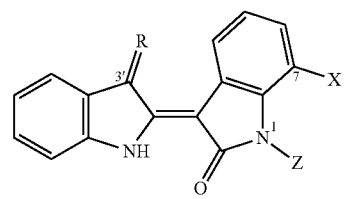

wherein,

R is selected from the group consisting of

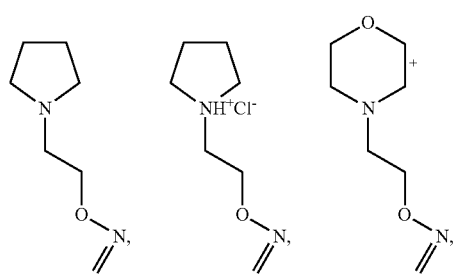

-continued

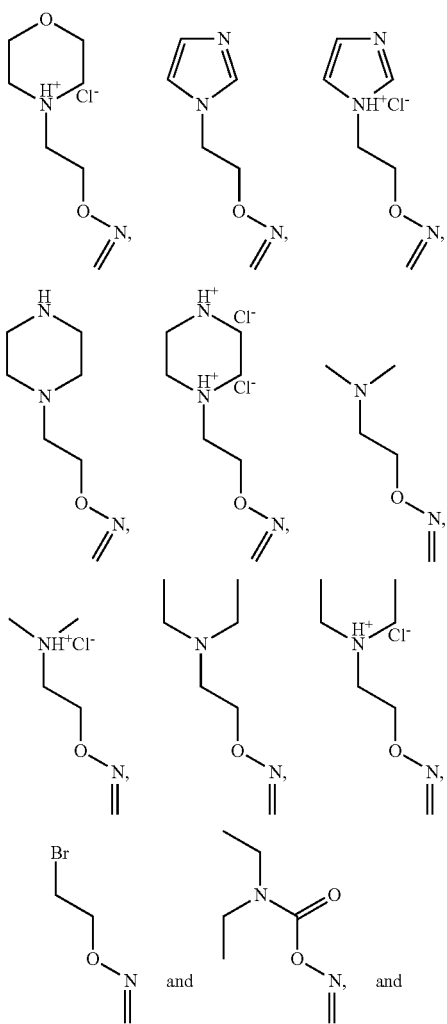

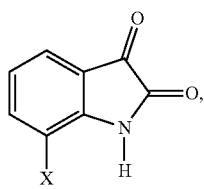 and

X is an halogen atom selected in the group comprising F, Cl, Br, and I, and Z is H or CH₃, or a salt thereof.

5. An Indirubin derivative according to claim 1, wherein X represents Br and Z is H.

6. A process for making 7-substituted indirubin-3'-oxime derivatives comprising:—a dimerization reaction of an appropriately substituted isatin derivative of the following formula

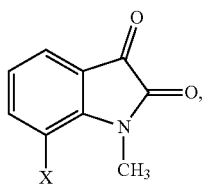

wherein X represents H, F, Cl, Br or I.

7. The process of claim 6, wherein said isatin derivatives are obtained through a two step procedure, using 7-halogeno-anilines as starting material, a first step, comprising reacting aniline derivatives of the following formula

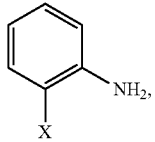

wherein X represents H, F, Cl, Br or I
with chloral hydrate and hydroxylamine hydrochloride to give the corresponding isonitrosoacetanilides, a second step, comprising heating the intermediate isonitrosoacetanilides under acidic conditions to give the 7-halogeno-isatines, 7-halogeno-N-methylisatines being prepared from the 7-halogeno-isatines, by treatment with dimethyl sulfate and Na₂CO₃.

8. The process of claim 6, comprising reacting substituted isatins, 7-halogeno-isatines or 7-halogeno-N-methylisatines of the following formula

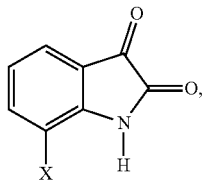

wherein X represents H, F, Cl, Br or I or of the following formula

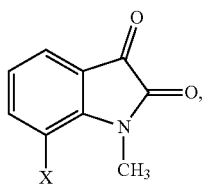

wherein X represents H, F, Cl, Br or I with 3-acetoxyindole in alkaline medium to give the corresponding bis-indoles.

9. The process of claim 6, wherein the oximes are prepared selectively in a (2'Z, 3'E) form by reacting appropriate indirubin derivatives with hydroxylamine hydrochloride in an organic solvent under reflux or methoxyamine hydrochloride, the acetoximes being prepared from the oximes with acetic anhydride in pyridine.

10. A process for preparing 3'-substituted oximes of 7-bromoindirubin-3'-oxime (7BIO) and 1-methyl-7-bromoindirubin-3'-oxime (Me7BIO) comprising reacting 3'-[O-(2-bromoethyl)oxime] intermediates with an amine.

11. A pharmaceutical composition comprising an effective amount of at least a 3'-, 7-substituted indirubin derivative according to claim 1, in combination with a pharmaceutically acceptable carrier.

12. The pharmaceutical compositions according to claim 11, which are formulated to be administered under oral, injectable, parental routes, with individual doses appropriate for the patient to be treated.

13. The pharmaceutical compositions according to claim 11, for treating human tumors which have developed apoptosis resistance mechanisms.

14. A derivative of claim 3 wherein alkyl is $C_1$-$C_3$ alkyl.

15. A derivative of claim 14 wherein R is a N—O—$CH_3$ radical.

16. A process of claim 10 wherein the amine is selected from the group consisting of pyrrolidine, morpholine, piperazine, imidazol, dimethylamine and diethylamine.

* * * * *